(12) United States Patent
Mori

(10) Patent No.: US 7,763,700 B2
(45) Date of Patent: Jul. 27, 2010

(54) EPOXY RESIN CURING COMPOSITION

(75) Inventor: Takahiro Mori, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 12/280,418

(22) PCT Filed: Mar. 14, 2007

(86) PCT No.: PCT/JP2007/055106

§ 371 (c)(1),
(2), (4) Date: Aug. 22, 2008

(87) PCT Pub. No.: WO2007/111136

PCT Pub. Date: Oct. 4, 2007

(65) Prior Publication Data

US 2009/0253887 A1    Oct. 8, 2009

(30) Foreign Application Priority Data

Mar. 28, 2006    (JP) ............................. 2006-087843

(51) Int. Cl.
*C08G 59/40* (2006.01)
(52) U.S. Cl. ......................... 528/96; 548/219
(58) Field of Classification Search ................ 528/96
See application file for complete search history.

(56) References Cited

U.S. PATENT DOCUMENTS 5,270,432 A    12/1993    Hergenrother et al.
2007/0293588 A1*  12/2007    Yoshida et al. ............... 516/31

FOREIGN PATENT DOCUMENTS

| JP | 11-504928 | 5/1999 |
|---|---|---|
| JP | 2001-31784 | 2/2001 |
| JP | 2001-39034 | 2/2001 |
| JP | 2001-49082 | 2/2001 |
| JP | 2003-213086 | 7/2003 |
| JP | 2004-524289 | 8/2004 |
| JP | 2005-29720 | 2/2005 |
| JP | 2005-514382 | 5/2005 |
| JP | 2005-179404 | 7/2005 |
| JP | 2005-520794 | 7/2005 |
| WO | WO 2004/010996 | 2/2004 |
| WO | WO 2004/072053 | 8/2004 |
| WO | WO 2005059001 A1 * | 6/2005 |

* cited by examiner

Primary Examiner—Mark Eashoo
Assistant Examiner—David Karst
(74) Attorney, Agent, or Firm—Young & Thompson

(57) ABSTRACT

An epoxy resin curing composition containing a compound having a benzoxazole structure represented by formula (I):

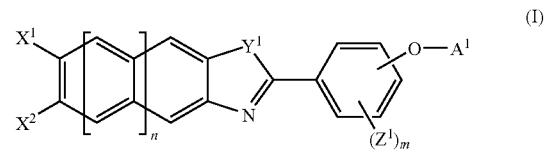

wherein $X^1$ and $X^2$, which may be the same or different, each represent hydrogen, a substituent having a phenolic hydroxyl group, or a substituent having an epoxy group, provided that $X^1=X^2\neq H$; or $X^1$ and $X^2$ are taken together to form a 3- to 8-membered, saturated or unsaturated heterocyclic ring substituted with a substituent having a phenolic hydroxyl group or a substituent having an epoxy group; $Y^1$ represents oxygen or sulfur; $Z^1$ represents a substituted or unsubstituted C1-C8 hydrocarbon group or a substituted or unsubstituted C1-C8 alkoxy group; m is an integer of 0 to 4; when m is 2 to 4, a plurality of $Z^1$s may be the same or different; n is an integer of 0 to 2; and $A^1$ represents hydrogen, a substituent having a phenolic hydroxyl group or a substituent having an epoxy group.

6 Claims, 5 Drawing Sheets

[Fig. 1]
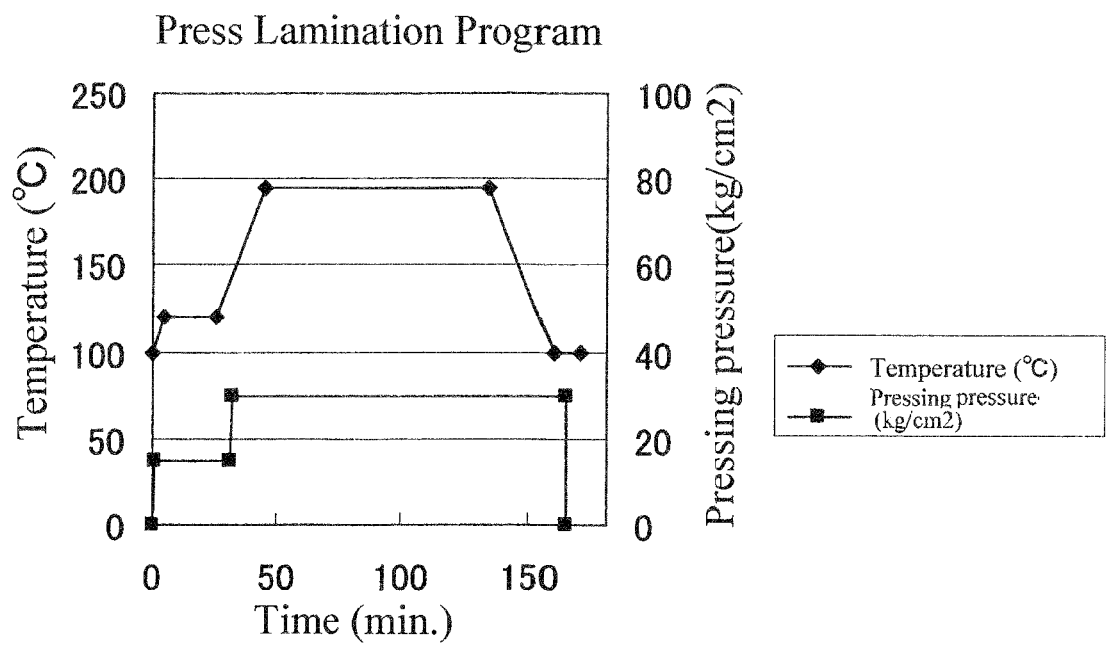

[Fig. 2]
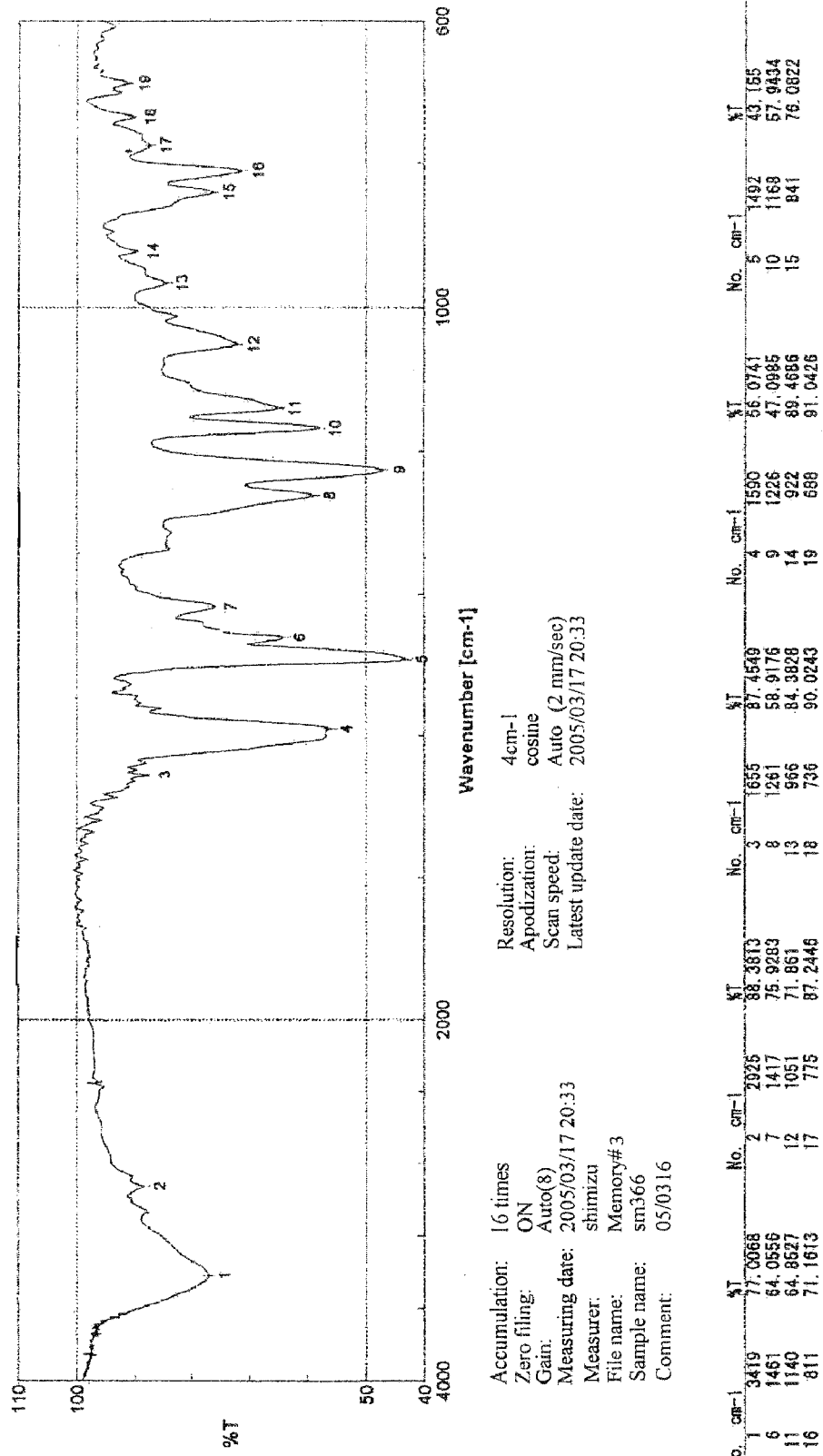

[Fig. 3]
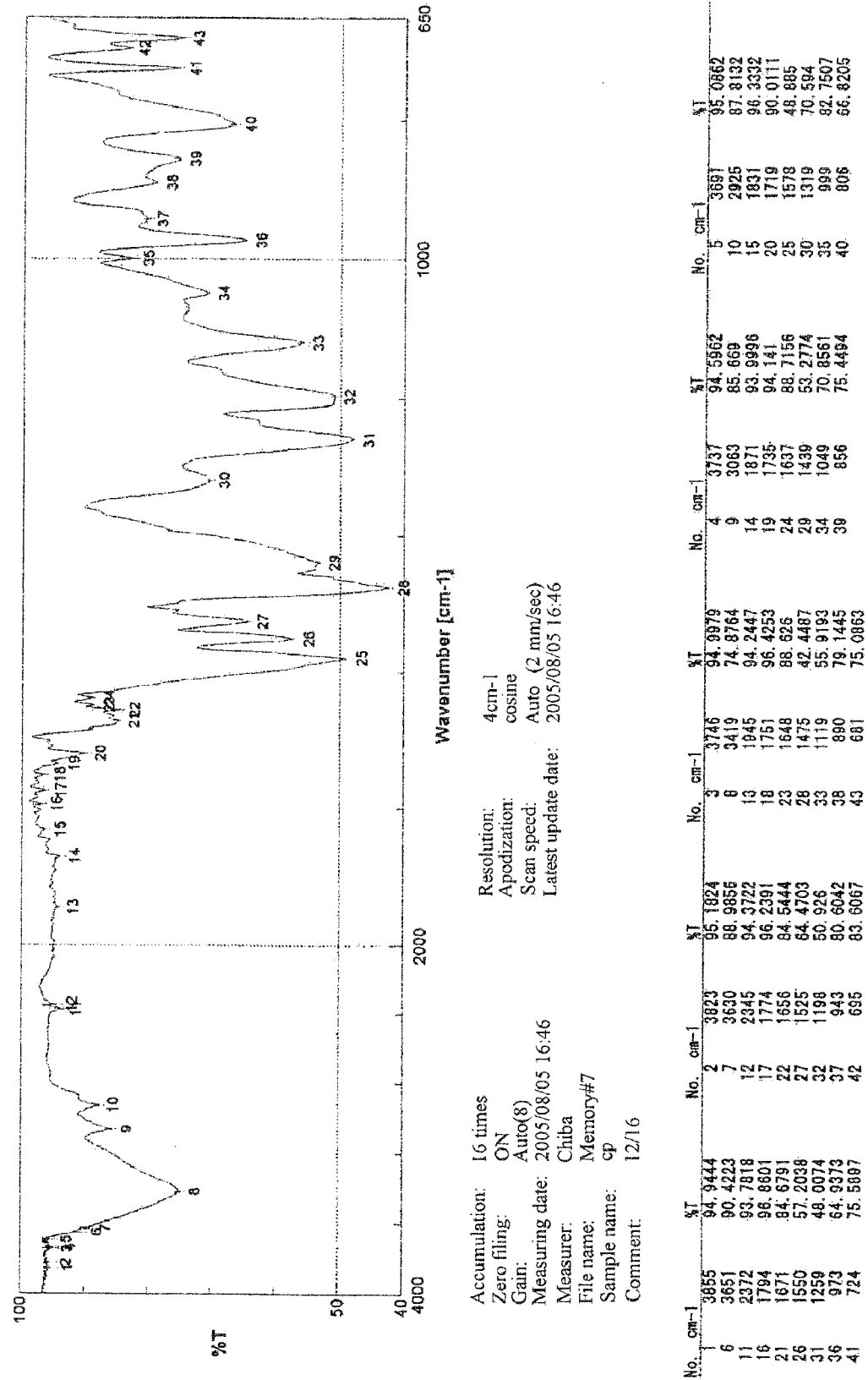

[Fig. 4]
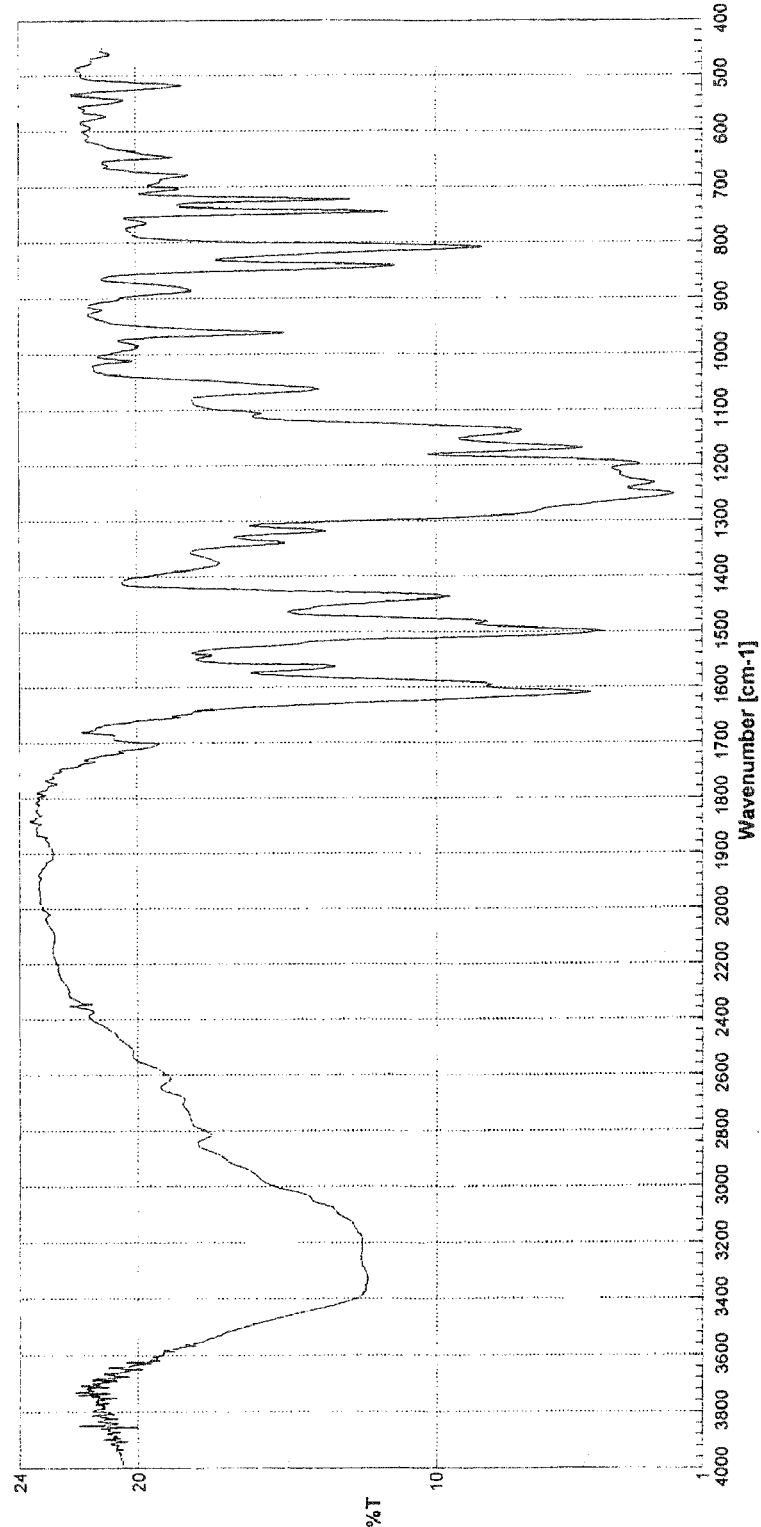

[Fig. 5]
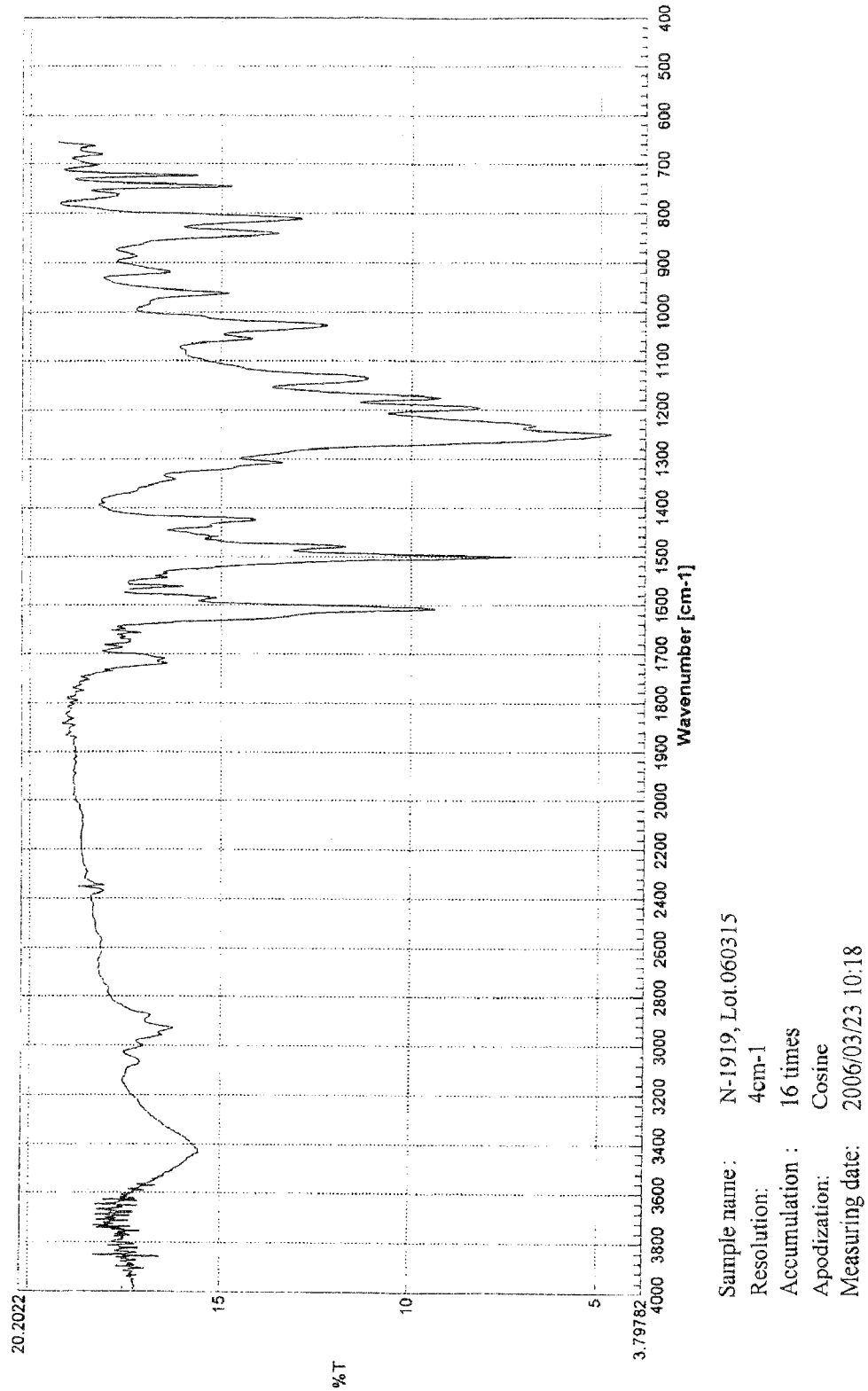

EPOXY RESIN CURING COMPOSITION

TECHNICAL FIELD

This invention relates to an epoxy resin curing composition containing a phenol compound having a benzoxazole structure or an epoxy compound having a benzoxazole structure. More particularly, it relates to an epoxy resin curing composition that contains a phenol compound having a benzoxazole structure as an epoxy resin curing agent or an epoxy compound having a benzoxazole structure as an epoxy resin and has a small coefficient of linear expansion and high tensile strength. The invention also relates to a novel compound having a benzoxazole structure.

An epoxy resin has been widely used to produce printed wiring boards (PWBs) because of its characteristics. Development of an epoxy resin that will respond the recent demands for high-density PWBs has been studied to cope with the demands for size and weight reduction.

A plating resist that remains on a PWB as an insulating layer as used in a build-up PWB is required to have high glass transition temperature, volume resistivity, mechanical characteristics, and low water absorption so as to response heat generation by highly integrated wiring, a decreasing thickness of an insulator layer, and reduction of adhesive strength between a conductor layer and an insulator layer.

An epoxy resin for use in prepregs has its linear expansion reduced by incorporating therein an inorganic filler of various types to have controlled thermal deformation. However, addition of an inorganic filler is disadvantageous in that tensile strength or elongation may reduce, or the filler may agglomerate to cause a short circuit, which ruins the reliability of the circuit.

Bisphenol A diglycidyl ether is widely known as a general-purpose epoxy resin. It is also widely known that polyphenol compounds such as phenol novolak are useful as an epoxy resin curing agent.

Non Patent Document 1 recites a variety of phenol curing agents, introducing a p-hydroxyphenyl maleimide/butyl acrylate copolymer as an epoxy resin curing agent having a phenol added to a heterocyclic condensed ring.

Patent Document 1, Patent Document 2, and Patent Document 3 disclose an epoxy resin composition containing a phenolic hydroxyl-containing polyamide resin and an epoxy resin.

These conventional epoxy resin compositions were insufficient in such physical properties as linear expansion coefficient, tensile strength, and elongation.

Patent Document 4 discloses a phenol compound having a benzoxazole structure, which is not used as a curing agent of an epoxy compound. Moreover, the resulting polymer is not an epoxy resin.

Patent Document 1: JP 2001-31784A

Patent Document 2: JP 2001-49082A

Patent Document 3: JP 2005-29720A

Patent Document 4: U.S. Pat. No. 5,270,432

Non Patent Document 1: *Epoxy jJushi Koukazai no Shintenkai*, CMC Publishing Co., Ltd.; p. 154 (1994) Disclosure of the Invention

Problem to be Solved by the Invention

An object of the present invention is to provide an epoxy resin curing composition that is free of a filler and yet excellent in physical properties including linear expansion coefficient, tensile strength, and elongation.

Means for Solving the Problem

In the light of the above circumstances, the present inventors have conducted extensive investigations and found as a result that an epoxy resin curing composition with excellent physical properties such as a low linear expansion coefficient, high tensile strength, and good elongation can be obtained by using a phenol compound having a benzoxazole structure as an epoxy resin curing agent or using an epoxy compound having a benzoxazole structure as an epoxy resin.

The above object of the invention is accomplished by the provision of an epoxy resin curing composition containing a compound having a benzoxazole structure represented by general formula (I):

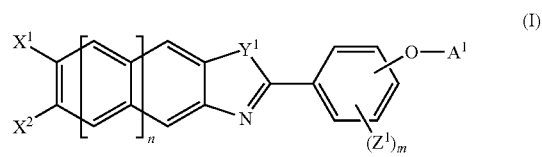

wherein $X^1$ and $X^2$, which may be the same or different, each independently represent a hydrogen atom, a substituent having a phenolic hydroxyl group, or a substituent having an epoxy group, with proviso that $X^1$ and $X^2$ do not represent a hydrogen atom at the same time; or $X^1$ and $X^2$ are linked to each other to form a 3- to 8-membered, saturated or unsaturated heterocyclic ring substituted with a substituent having a phenolic hydroxyl group or a substituent having an epoxy group; $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

Preferably, the object of the invention is accomplished by the epoxy resin curing composition wherein either one of $X^1$ and $X^2$ is represented by general formula (Ia):

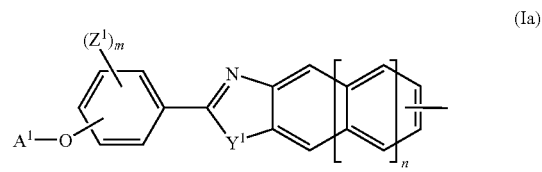

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

Preferably, the object of the invention is accomplished by the epoxy resin curing composition wherein either one of $X^1$ and $X^2$ is represented by general formula (Ib):

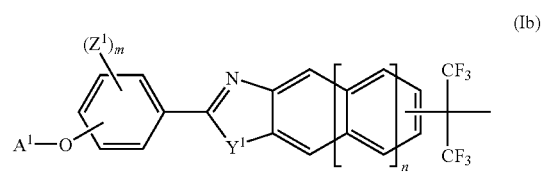

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

Preferably, the object of the invention is accomplished by the epoxy resin curing composition wherein $X^1$ and $X^2$ are linked to each other to form a heterocyclic ring represented by general formula (Ic) or (Id):

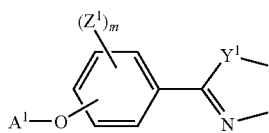

(Ic)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; and $A^1$ represents a hydrogen atom, a substituent having a phenolic hydroxyl group or a substituent having an epoxy group.

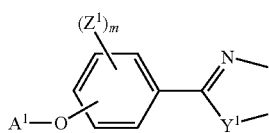

(Id)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; and $A^1$ represents a hydrogen atom, a substituent having a phenolic hydroxyl group or a substituent having an epoxy group.

Preferably, the object of the invention is accomplished by the epoxy resin curing composition wherein $A^1$ is a substituent having an epoxy group.

The object of the invention is also accomplished by the provision of an epoxy resin curing composition containing a compound having a benzoxazole structure represented by general formula (II):

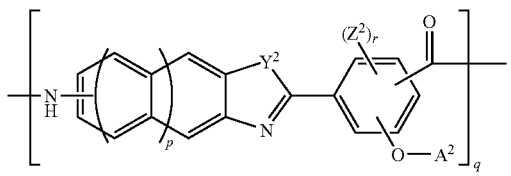

(II)

wherein $Y^2$ represents an oxygen atom or a sulfur atom; $Z^2$ represents a substituted or unsubstituted hydrocarbon group having 1 to 8 carbon atoms or a substituted or unsubstituted alkoxy group having 1 to 8 carbon atoms; r represents an integer of 0 to 3; when r is 2 or 3, a plurality of $Z^2$s may be the same or different; p represents an integer of 0 to 2; q represents a number of 1 to 100; and $A^2$ represents a hydrogen atom, a substituent having a phenolic hydroxyl group or a substituent having an epoxy group.

The object of the invention is also accomplished by the provision of an epoxy resin curing composition containing a compound having a benzoxazole structure represented by general formula (III):

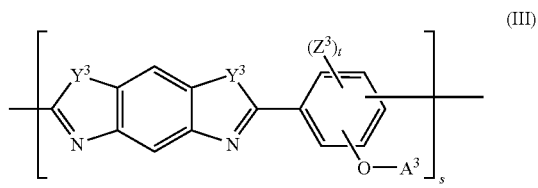

(III)

wherein $Y^3$ represents an oxygen atom or a sulfur atom; $Z^3$ represents a substituted or unsubstituted hydrocarbon group having 1 to 8 carbon atoms or a substituted or unsubstituted alkoxy group having 1 to 8 carbon atoms; t represents an integer of 0 to 3; when t is 2 or 3, a plurality of $Z^3$s may be the same or different; s represents a number of 1 to 100; and $A^3$ represents a hydrogen atom, a substituent having a phenolic hydroxyl group or a substituent having an epoxy group.

The object of the invention is also accomplished by the provision of an epoxy resin curing composition containing a compound having a benzoxazole structure represented by general formula (IV):

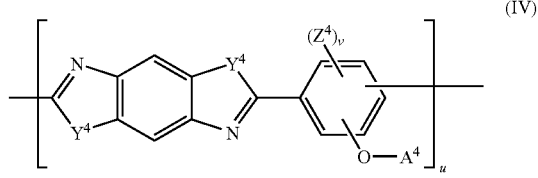

(IV)

wherein $Y^4$ represents an oxygen atom or a sulfur atom; $Z^4$ represents a substituted or unsubstituted hydrocarbon group having 1 to 8 carbon atoms or a substituted or unsubstituted alkoxy group having 1 to 8 carbon atoms; v represents an integer of 0 to 3; when v is 2 or 3, a plurality of $Z^4$s may be the same or different; u represents a number of 1 to 100; and $A^4$ represents a hydrogen atom, a substituent having a phenolic hydroxyl group or a substituent having an epoxy group.

Preferably, the object of the invention is accomplished by the epoxy resin curing composition wherein $A^2$ in general formula (II)), $A^3$ in general formula (III), or $A^4$ in general formula (IV) is a substituent having an epoxy group.

The object of the invention is also accomplished by the provision of a curing composition for a laminated sheet comprising the above described epoxy resin curing composition.

The object of the invention is also accomplished by the provision of a cured product obtained by curing the above described epoxy resin curing composition.

The object of the invention is also accomplished by the provision of a novel benzoxazole compound represented by general formula (V):

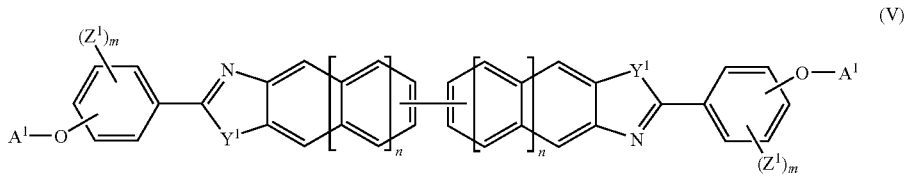

(V)

wherein $Y^1$ represents an oxygen atom or a sulfur atom, $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a substituent having a phenolic hydroxyl group or a substituent having an epoxy group.

The object of the invention is also accomplished by the provision of a novel benzoxazole compound represented by general formula (VI):

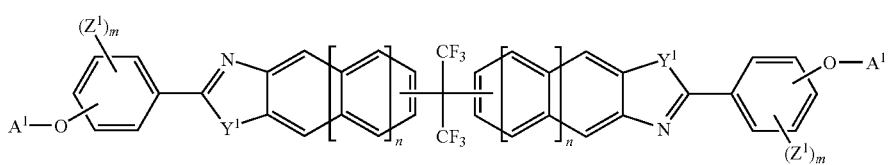

(VI)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a substituent having a phenolic hydroxyl group or a substituent having an epoxy group.

BRIEF DESCRIPTION OF THE DRAWING

FIG. 1 is a diagram showing the laminating conditions of vacuum pressing.
FIG. 2 is an IR chart of compound No. 12.
FIG. 3 is an IR chart of compound No. 13.
FIG. 4 is an IR chart of compound No. 4.
FIG. 5 is an IR chart of compound No. 14.

BEST MODE FOR CARRYING OUT THE INVENTION

The present invention will be described with reference to its preferred embodiments.

The epoxy resin curing composition of the invention contains a compound having a benzoxazole structure represented by general formula (I):

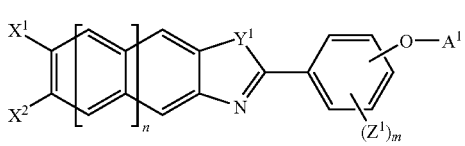

(I)

wherein $X^1$ and $X^2$, which may be the same or different, each independently represent a hydrogen atom, a substituent having a phenolic hydroxyl group, or a substituent having an epoxy group, with proviso that $X^1$ and $X^2$ do not represent a hydrogen atom at the same time; or $X^1$ and $X^2$ are linked to each other to form a 3- to 8-membered, saturated or unsaturated heterocyclic ring substituted with a substituent having a phenolic hydroxyl group or a substituent having an epoxy group; $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

In general formula (I), the term "substituent having a phenolic hydroxyl group" denotes any substituent having a phenolic hydroxyl group including a phenol group. The substituent having a phenolic hydroxyl group is exemplified by a substituent represented by general formula (VII):

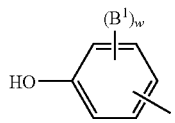

(VII)

wherein $B^1$ represents a substituent; and w represents a number of 0 to 4; when w is 2 to 4, a plurality of $B^1$s may be the same or different; the substituent $B^1$ is not particularly limited and includes an alkyl group, an alkoxy group, an aryl group, or a like organic group.

The substituent having a phenolic hydroxyl group is preferably a phenol group, i.e., the group of general formula (VII) in which w=0, in view of the production cost and physical properties of a cured product such as thermal linear expansion.

The term "substituent having an epoxy group" as referred to in general formula (I) denotes any group having an epoxy group and may have other substituent(s). Examples of the substituent having an epoxy group include an epoxy group, an alicyclic epoxy group, a glycidyl group, and a glycidyl-containing substituent represented by general formula (VIII):

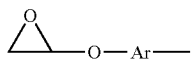
(VIII)

wherein Ar represents a substituted or unsubstituted alkylene group or a substituted or unsubstituted arylene group, the alkylene or arylene group may be interrupted by an unsaturated bond, an ether bond, a thioether bond or an ester bond.

Examples of the alkylene or arylene group include methylene, ethylene, propylene, butylene, and phenylene. An alkylene group or a phenylene group are preferred of them in view of the production cost, reactivity, and physical properties of a cured product such as thermal linear expansion coefficient and a glass transition point.

The substituent having an epoxy group is preferably a glycidyl group or a glycidyl-containing substituent represented by general formula (VIII) in view of the production cost and physical properties.

In general formula (I), $Z^1$ represents a substituted or unsubstituted hydrocarbon group having 1 to 8 carbon atoms or a substituted or unsubstituted alkoxy group having 1 to 8 carbon atoms, and m represents an integer of 0 to 4. When m is 2 to 4, a plurality of $Z^1$s may be the same or different. m is preferably 0 in view of the production cost and physical properties.

Examples of the substituted or unsubstituted hydrocarbon group having 1 to 8 carbon atoms include an alkyl group such as methyl, ethyl, and isopropyl; a cycloalkyl group such as cyclohexyl; and an aryl group such as phenyl. Examples of the substituent of the hydrocarbon group include a halogen atom, a trifluoromethyl group, an alkoxy group (e.g., methoxy), and a hydroxyl group. Examples of the substituted or unsubstituted alkoxy group having 1 to 8 carbon atoms include a phenyl ether group, an alkyl ether group, a phenoxy group, and a methoxy group. Examples of the substituent of the alkoxy group include a halogen atom, a trifluoromethyl group, a hydroxyl group, and a methoxy group.

$X^1$ and $X^2$ may be linked to each other to form a 3- to 8-membered, saturated or unsaturated heterocyclic ring. The saturated or unsaturated heterocyclic ring has a substituent having a phenolic hydroxyl group or a substituent having an epoxy group. Examples of the saturated heterocyclic ring include morpholine, and examples of the unsaturated heterocyclic ring include oxazole and thiazole.

Of the compounds having a benzoxazole structure represented by general formula (I) preferred are those in which either one of $X^1$ and $X^2$ is a group represented by general formula (Ia) shown below in view of the production cost, reactivity, and physical properties of a cured product such as thermal linear expansion coefficient and glass transition point.

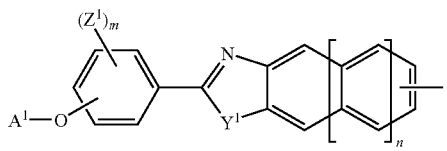
(Ia)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

The term "substituent having a phenolic hydroxyl group" and the term "substituent having an epoxy group" as used in general formula (Ia) have the same meaning as respectively described as for general formula (I). Preference for these groups is the same as in general formula (I). Similarly to general formula (I), m is preferably 0.

Also preferred compounds having a benzoxazole structure represented by general formula (I) are those in which either one of $X^1$ and $X^2$ is a group represented by general formula (Ib) shown below in view of the production cost, reactivity, and physical properties of a cured product such as thermal linear expansion coefficient and glass transition point.

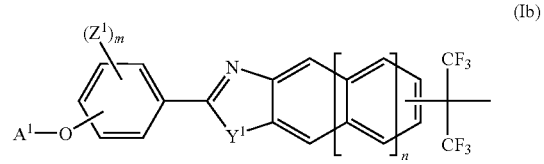
(Ib)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

The term "substituent having a phenolic hydroxyl group" and the term "substituent having an epoxy group" as used in general formula (Ib) have the same meaning as respectively described as for general formula (I). Preference for these groups is the same as in general formula (I). Similarly to general formula (I), m is preferably 0.

Also preferred compounds having a benzoxazole structure represented by general formula (I) are those in which $X^1$ and $X^2$ are linked to each other to form a heterocyclic ring represented by general formula (Ic) or (Id) shown below in view of the production cost, reactivity, and physical properties of a cured product such as thermal linear expansion coefficient and glass transition point.

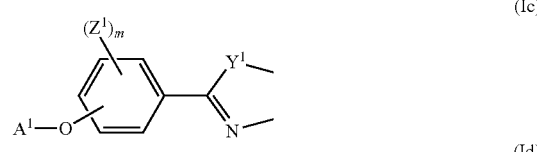
(Ic)

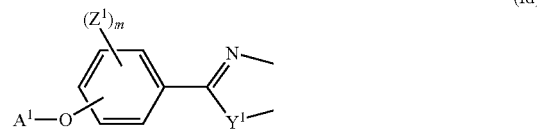
(Id)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; and $A^1$ represents a hydrogen atom, a substituent having a phenolic hydroxyl group or a substituent having an epoxy group.

The term "substituent having a phenolic hydroxyl group" and the term "substituent having an epoxy group" as used in general formula (Ic) or (Id) have the same meaning as respectively described as for general formula (I). Preference for these groups is the same as in general formula (I). Similarly to general formula (I), m is preferably 0.

The 3- to 8-membered, saturated or unsaturated heterocyclic ring formed by linkage of $X^1$ and $X^2$ is preferably a 5-membered unsaturated heterocyclic ring in view of the production cost and reactivity of the compound and the physical properties of a cured product such as thermal linear expansion coefficient and glass transition point.

When the compound having a benzoxazole structure represented by general formula (I) is a compound having a phenolic hydroxyl group, $A^1$ is a substituent having a phenolic hydroxyl group (including a phenol group) or a hydrogen atom. When the compound having a benzoxazole structure represented by general formula (I) is a compound having an epoxy group, $A^1$ is a substituent having an epoxy group (inclusive of an epoxy group).

In the case where the compound having a benzoxazole structure represented by general formula (I) is a compound having a phenolic hydroxyl group, the compound is preferably used as a curing agent for epoxy resins (hereinafter also referred to as a phenol curing agent). The amount of the compound in an epoxy resin curing composition is preferably 10% to 90% by mass, more preferably 30% to 80% by mass.

In the case where the compound having a benzoxazole structure represented by general formula (I) is a compound having an epoxy group, the compound is preferably used as an epoxy component (hereinafter also referred to as an epoxy resin). The amount of the compound in an epoxy resin curing composition is preferably 10% to 90% by mass, more preferably 30% to 80% by mass.

The compound of general formula (II) will then be described. The epoxy resin curing composition of the invention contains the compound having a benzoxazole structure represented by general formula (II).

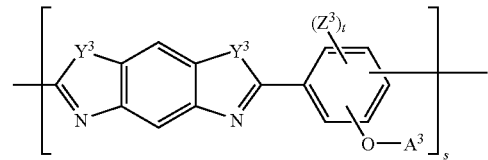

(II)

wherein $Y^2$ represents an oxygen atom or a sulfur atom; $Z^2$ represents a substituted or unsubstituted hydrocarbon group having 1 to 8 carbon atoms or a substituted or unsubstituted alkoxy group having 1 to 8 carbon atoms; r represents an integer of 0 to 3; when r is 2 or 3, a plurality of $Z^2$s may be the same or different; p represents an integer of 0 to 2; q represents a number of 1 to 100; and $A^2$ represents a hydrogen atom, a substituent having a phenolic hydroxyl group or a substituent having an epoxy group.

In formula (II), the term "substituent having a phenolic hydroxyl group" and the term "substituent having an epoxy group" have the same meaning as respectively described as for general formula (I). Preference for these groups is the same as in general formula (I). r is preferably 0 in view of the production cost and physical properties. q is preferably 1 to 10 in view of the production cost, solubility in solvent, affinity to resin, and reactivity.

When the compound having a benzoxazole structure represented by general formula (II) is a compound having a phenolic hydroxyl group, $A^2$ is a substituent having a phenolic hydroxyl group (including a phenol group) or a hydrogen atom. When the compound having a benzoxazole structure represented by general formula (II) is a compound having an epoxy group, $A^2$ is a substituent having an epoxy group (including an epoxy group).

In the case where the compound having a benzoxazole structure represented by general formula (II) is a compound having a phenolic hydroxyl group, the compound is preferably used as a curing agent for epoxy resins (hereinafter also referred to as a phenol curing agent). The amount of the compound in an epoxy resin curing composition is preferably 10% to 90% by mass, more preferably 30% to 80% by mass.

In the case where the compound having a benzoxazole structure represented by general formula (II) is a compound having an epoxy group, the compound is preferably used as an epoxy component (hereinafter also referred to as an epoxy resin). The amount of the compound in an epoxy resin curing composition is preferably 10% to 90% by mass, more preferably 30% to 80% by mass.

The compound of general formula (III) will then be described. The epoxy resin curing composition of the invention contains the compound having a benzoxazole structure represented by general formula (III).

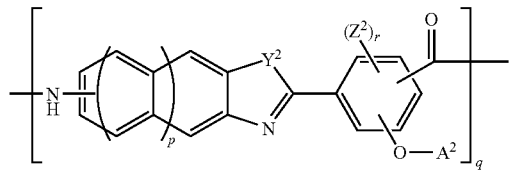

(III)

wherein $Y^3$ represents an oxygen atom or a sulfur atom; $Z^3$ represents a substituted or unsubstituted hydrocarbon group having 1 to 8 carbon atoms or a substituted or unsubstituted alkoxy group having 1 to 8 carbon atoms; t represents an integer of 0 to 3; when t is 2 or 3, a plurality of $Z^3$s may be the same or different; s represents a number of 1 to 100; and $A^3$ represents a hydrogen atom, a substituent having a phenolic hydroxyl group or a substituent having an epoxy group.

In formula (III), the term "substituent having a phenolic hydroxyl group" and the term "substituent having an epoxy group" have the same meaning as respectively described as for general formula (I). Preference for these groups is the same as in general formula (I). t is preferably 0 in view of the production cost and physical properties. s is preferably 1 to 10 in view of the production cost, solubility in solvent, affinity to resin, and reactivity.

When the compound having a benzoxazole structure represented by general formula (III) is a compound having a phenolic hydroxyl group, $A^3$ is a substituent having a phenolic hydroxyl group (including a phenol group) or a hydrogen atom. When the compound having a benzoxazole structure represented by general formula (III) is a compound having an epoxy group, $A^3$ is a substituent having an epoxy group (including an epoxy group).

In the case where the compound having a benzoxazole structure represented by general formula (III) is a compound having a phenolic hydroxyl group, the compound is preferably used as a curing agent for epoxy resins (hereinafter also referred to as a phenol curing agent). The amount of the compound in an epoxy resin curing composition is preferably 10% to 90% by mass, more preferably 30% to 80% by mass.

In the case where the compound having a benzoxazole structure represented by general formula (III) is a compound having an epoxy group, the compound is preferably used as an epoxy component (hereinafter also referred to as an epoxy resin). The amount of the compound in an epoxy resin curing composition is preferably 10% to 90% by mass, more preferably 30% to 80% by mass.

The compound of general formula (IV) will be described. The epoxy resin curing composition of the invention contains the compound having a benzoxazole structure represented by general formula (IV).

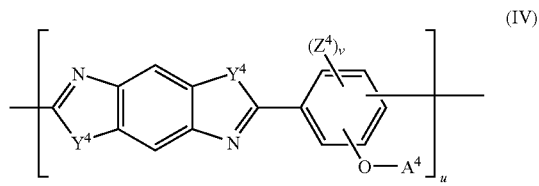

wherein $Y^4$ represents an oxygen atom or a sulfur atom; $Z^4$ represents a substituted or unsubstituted hydrocarbon group having 1 to 8 carbon atoms or a substituted or unsubstituted alkoxy group having 1 to 8 carbon atoms; v represents an integer of 0 to 3; when v is 2 or 3, a plurality of $Z^4$s may be the same or different; u represents a number of 1 to 100; and $A^4$ represents a hydrogen atom, a substituent having a phenolic hydroxyl group or a substituent having an epoxy group.

In formula (IV), the term "substituent having a phenolic hydroxyl group" and the term "substituent having an epoxy group" have the same meaning as respectively described as for general formula (I). Preference for these groups is the same as in general formula (I). v is preferably 0 in view of the production cost and physical properties. u is preferably 1 to 10 in view of the production cost, solubility in solvent, affinity to resin, and reactivity.

When the compound having a benzoxazole structure represented by general formula (IV) is a compound having a phenolic hydroxyl group, $A^4$ is a substituent having a phenolic hydroxyl group (including a phenol group) or a hydrogen atom. When the compound having a benzoxazole structure represented by general formula (IV) is a compound having an epoxy group, $A^4$ is a substituent having an epoxy group (including an epoxy group).

In the case where the compound having a benzoxazole structure represented by general formula (IV) is a compound having a phenolic hydroxyl group, the compound is preferably used as a curing agent for epoxy resins (hereinafter also referred to as a phenol curing agent). The amount of the compound in an epoxy resin curing composition is preferably 10% to 90% by mass, more preferably 30% to 80% by mass.

In the case where the compound having a benzoxazole structure represented by general formula (IV) is a compound having an epoxy group, the compound is preferably used as an epoxy component (hereinafter also referred to as an epoxy resin). The amount of the compound in an epoxy resin curing composition is preferably 10% to 90% by mass, more preferably 30% to 80% by mass.

The compounds having a benzoxazole structure and a phenolic hydroxyl group will be described in more detail.

Specific examples of the compound represented by general formula (I) and having a phenolic hydroxyl group include compound Nos. 1 to 8 shown below. The compound represented by general formula (II) and having a phenolic hydroxyl group is exemplified by compound No. 9 shown below. The compound represented by general formula (III) and having a phenolic hydroxyl group is exemplified by compound No. 10-1 shown below. The compound represented by general formula (IV) and having a phenolic hydroxyl group is exemplified by compound No. 10-2 shown below. Understandably, these specific examples are only illustrative but not for limitation.

Compound No. 1

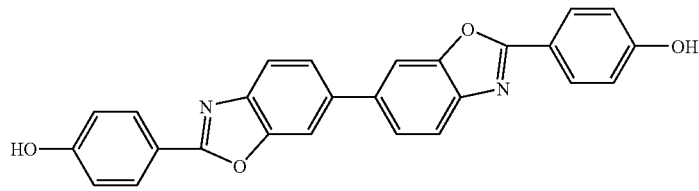

Compound No. 2

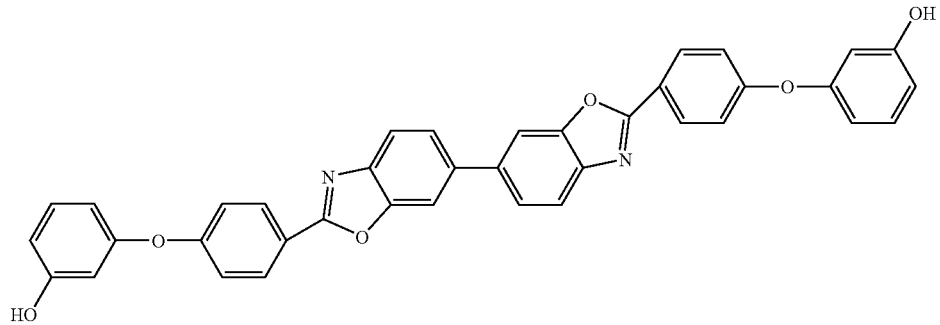

Compound No. 3

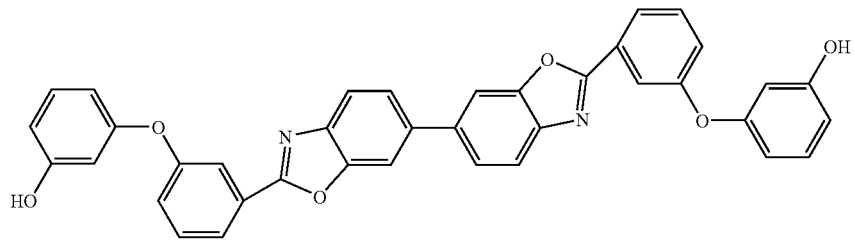

-continued

Compound No. 4

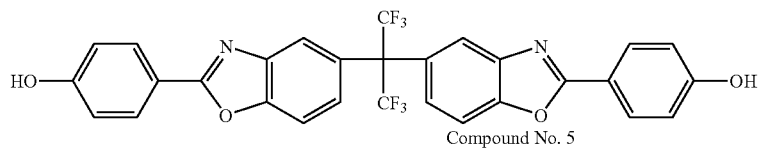

Compound No. 5

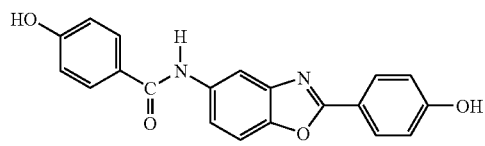

Compound No. 6

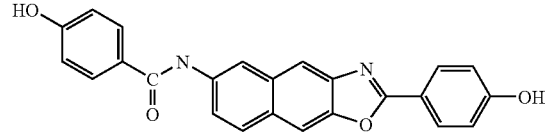

Compound No. 7

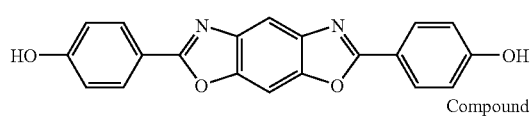

Compound No. 8

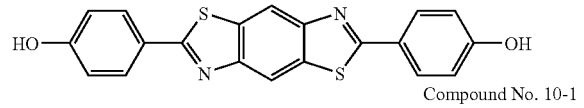

Compound No. 9

Compound No. 10-1

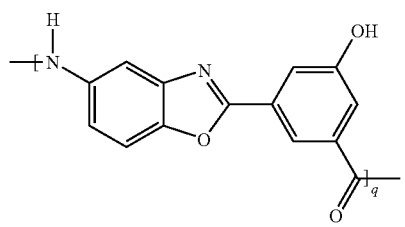

Compound No. 10-2

The compound represented by general formula (I) and having a phenolic hydroxyl group (hereinafter also referred to as a phenol compound) can be synthesized by forming an oxazine ring from a dihydroxybenzidine derivative and a benzoic acid derivative to obtain a compound having a benzoxazine structure. Taking compound No. 2 for instance, the synthesis starts with oxazine ring formation as shown in Reaction formula (A) below. That is, 3,3-dihydroxybenzidine and 4-fluorobnzoic acid are caused to react in a solvent to obtain a fluoro compound (i.e., 2,2'-bis(4-fluorophenyl)bis-benzoxazole), which is then etherified with resorcinol in a solvent in the presence of a base as shown in Reaction formula (B) below to give compound No. 3 (phenol compound).

Reaction formula A

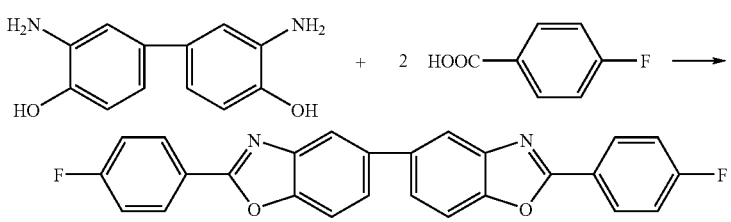

Reaction formula B

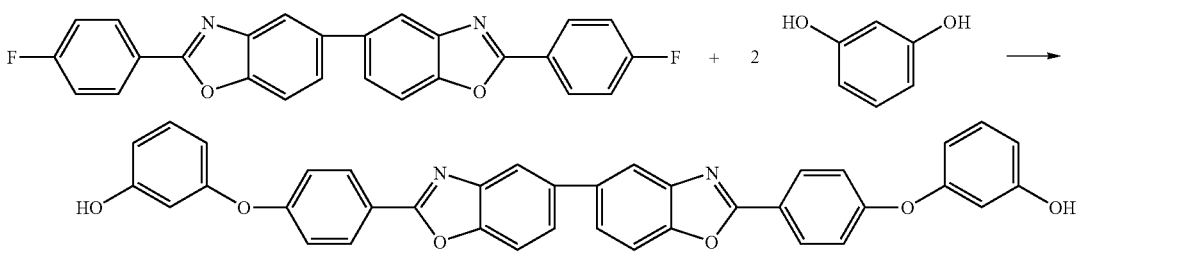

The compound represented by general formula (II) and having a phenolic hydroxyl group (hereinafter also referred to as a phenol compound) can be synthesized by direct polycondensation reaction between a diaminophenol derivative and a hydroxyphthalic acid derivative using a triphenyl phosphite-pyridine condensing agent, followed by heating to cause ring closure. For the details of direct polycondensation reaction using a triphenyl phosphite-pyridine condensing agent, reference can be made to The Chemical Society of Japan (ed.), *Jikken Kagaku Koza* 28, "Koubunshi Gousei", 4th Ed., Maruzen (1992). Going into detail taking compound No. 9 for instance, amidol and 5-hydroxyisophthalic acid are subjected to polycondensation in N-methylpyrrolidone in the presence of triphenyl phosphite, pyridine, and lithium chloride. After the reaction, the polycondensate is taken out and heated to cause ring closure.

The compound represented by general formula (III) or (IV) and having a phenolic hydroxyl group (hereinafter also referred to as a phenol compound) can be synthesized by direct polycondensation reaction between a diaminoresorcinol derivative and a hydroxyphthalic acid derivative using a triphenyl phosphite-pyridine condensing agent, followed by heating to cause ring closure. The direct polycondensation reaction is carried out in the same manner as described in connection with the compound represented by general formula (II) and having a phenolic hydroxyl group. Going into detail taking compound No. 10-1 for instance, 4,6-diaminoresorcinol dihydrochloride and 5-hydroxyisophthalic acid are subjected to polycondensation in N-methylpyrrolidone in the presence of triphenyl phosphite, pyridine, and lithium chloride. After the reaction, the polycondensate is taken out and heated to cause ring closure.

The compounds having a benzoxazole structure and an epoxy group will be described in detail.

Specific examples of the compound represented by general formula (I) and having an epoxy group include compound Nos. 11 to 18 shown below. The compound represented by general formula (II) and having an epoxy group is exemplified by compound No. 19 shown below. The compound represented by general formula (III) and having an epoxy group is exemplified by compound No. 20-1 shown below. The compound represented by general formula (IV) and having an epoxy group is exemplified by compound No. 20-2 shown below. Understandably, these specific examples are only illustrative but not for limitation.

Compound No. 11

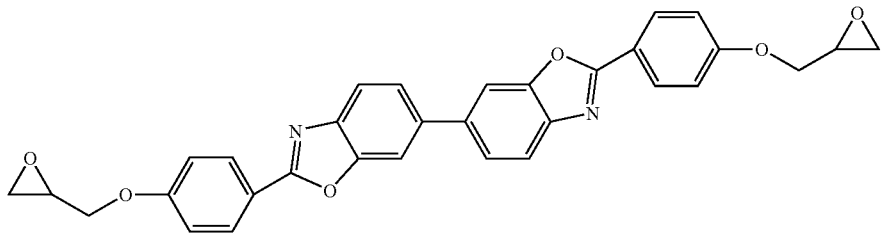

Compound No. 12

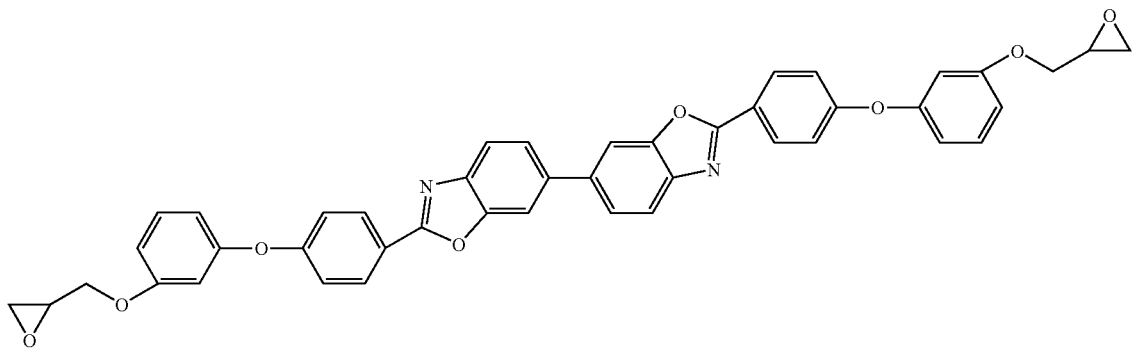

Compound No. 13

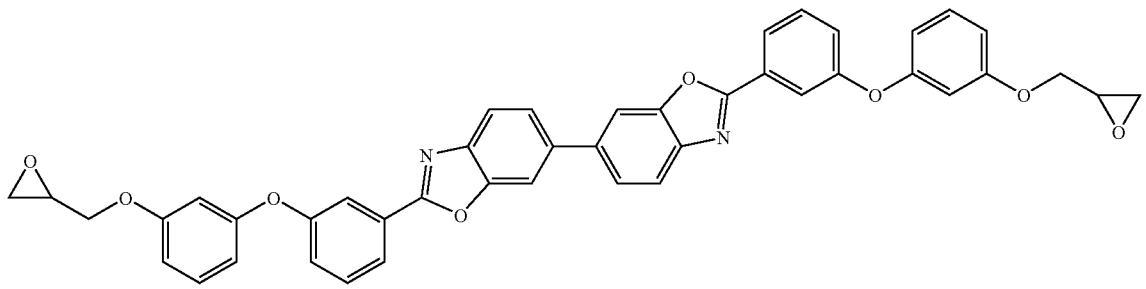

-continued

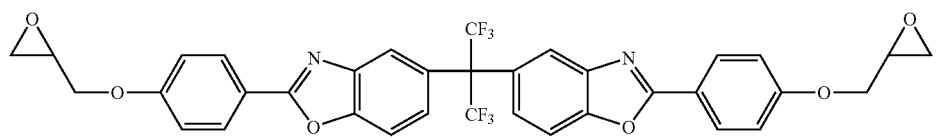
Compound No. 14

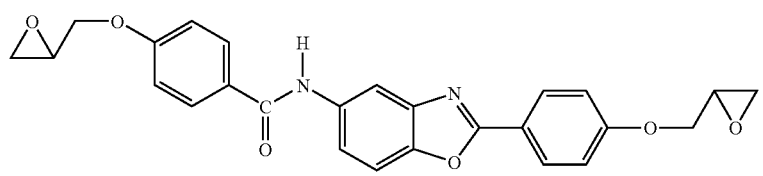
Compound No. 15

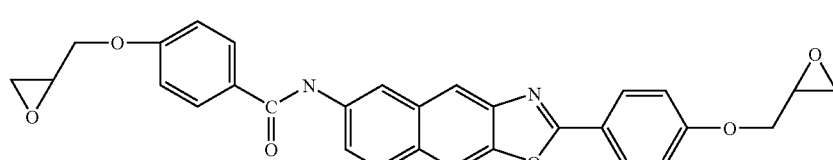
Compound No. 16

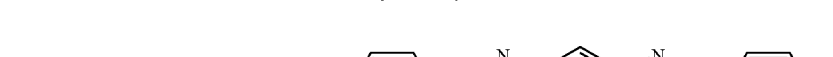
Compound No. 17

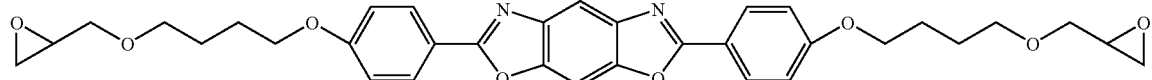
Compound No. 18

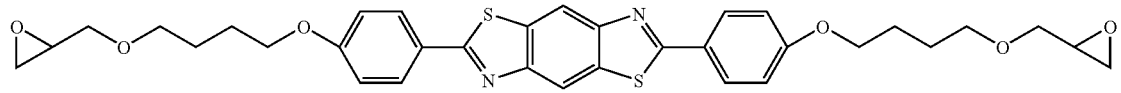
Compound No. 19

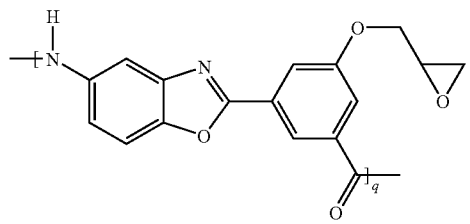
Compound No. 20-1

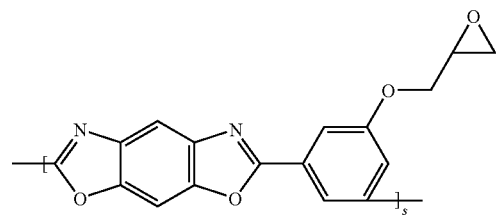
Compound No. 20-2

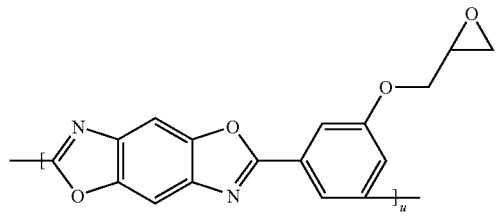

The compound represented by general formula (I) and having an epoxy group (hereinafter also referred to as an epoxy compound) can be synthesized by causing a compound represented by general formula (I) and having a phenolic hydroxyl group (phenol compound) and epichlorohydrin in a solvent in the presence of a base as exemplified by Reaction formula (C) below.

Reaction formula C

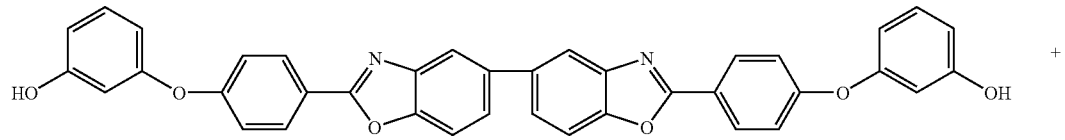
+

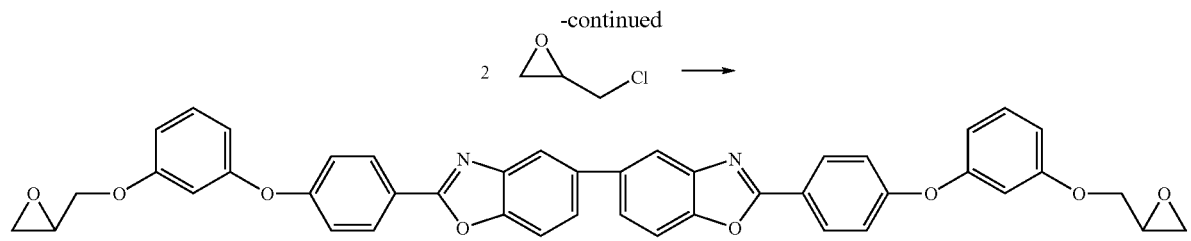

The compound represented by general formula (II), (III) or (IV) and having an epoxy group (hereinafter also referred to as an epoxy compound) can be obtained similarly by causing a corresponding compound represented by general formula (II), (III) or (IV), respectively, and having a phenolic hydroxyl group (phenol compound) with epichlorohydrin in a solvent in the presence of a base.

The epoxy resin curing compound of the invention may contain other known epoxy compound as an epoxy component when in using the compound having an epoxy group of the invention (epoxy compound) (i.e., the epoxy compound of general formula (I) (e.g., compound Nos. 11-18), the epoxy compound of general formula (II) (e.g., compound No. 19), the epoxy compound of general formula (III) (e.g., compound No. 20-1), or the epoxy compound of general formula (IV) (e.g., compound No. 20-2) as well as using the compound having a phenolic hydroxyl group of the invention (phenol compound) (i.e., the phenol compound of general formula (I), e.g., compound Nos. 1 to 8), the phenol compound of general formula (II) (e.g., compound No. 9), the phenol compound of general formula (III) (e.g., compound No. 10-1) or the phenol compound of general formula (IV) (e.g., compound No. 10-2) as a curing agent.

The other epoxy compound that can be used in the epoxy resin curing composition is not particularly limited. For example, known aromatic, alicyclic or aliphatic epoxy compounds can be used. Examples of the aromatic epoxy compounds include glycidyl ethers of polyhydric phenols such as hydroquinone, resorcinol, bisphenol A, bisphenol F, 4,4'-dihydroxybiphenyl, novolak, tetrabromobisphpenol A, and 2,2-bis(4-hydroxyphenyl)-1,1,1,3,3,3-hexafluoropropane. Examples of the alicyclic epoxy compounds include polyglycidyl ethers of polyhydric phenols having at least one alicyclic group, and cyclohexene oxide- or cyclopentene oxide-containing compounds obtained by epoxidizing cyclohexene ring- or cyclopentene ring-containing compounds with an oxidizing agent. Examples of such alicyclic epoxy compounds include hydrogenated bisphenol A diglycidyl ether, 3,4-epoxycyclohexylmethyl 3,4-epoxycyclohexylcarboxylate, 3,4-epoxy-1-methylcyclohexyl 3,4-epoxy-1-methylhexanecarboxylate, 6-methyl-3,4-epoxycyclohexylmethyl 6-methyl-3,4-epoxycyclohexanecarboxylate, 3,4-epoxy-3-methylcyclohexylmethyl 3,4-epoxy-3-methylcyclohexanecarboxylate, 3,4-epoxy-5-methylcyclohexylmethyl 3,4-epoxy-5-methylcyclohexanecarboxylate, bis(3,4-epoxycyclohexylmethyl)adipate, methylenebis(3,4-epoxycyclohexane), 2,2-bis(3,4-epoxycyclohexyl)propane, dicyclopentadiene diepoxide, ethylenebis(3,4-epoxycyclohexanecarboxylate), dioctyl epoxyhexahydrophthalate, and di-2-ethylhexyl epoxyhexahydrophthalate. The aliphatic epoxy compounds include a polyglycidyl ether of an aliphatic polyhydric alcohol or an alkylene oxide adduct thereof, an aliphatic long chain polybasic acid polyglycidyl ester, homopolymers obtained by vinyl polymerization of glycidyl acrylate or glycidyl methacrylate, and copolymers obtained by vinyl polymerization of glycidyl acrylate or glycidyl methacrylate with other vinyl monomer(s). Typical examples of such aliphatic epoxy compounds include polyhydric alcohol glycidyl ethers such as 1,4-butanediol diglycidyl ether, 1,6-hexanediol diglycidyl ether, glycerol triglycidyl ether, trimethylolpropane triglycidyl ether, sorbitol tetraglycidyl ether, dipentaerythritol hexaglycidyl ether, polyethylene glycol diglycidyl ether, and polypropylene glycol diglycidyl ether; polyglycidyl ethers of polyether polyols obtained by adding one or more kinds of an alkylene oxide to an aliphatic polyhydric alcohol, e.g., propylene glycol, trimethylolpropane or glycerol; and diglycidyl esters of aliphatic long chain dibasic acids. Additional examples of useful epoxy compounds include monoglycidyl ethers of aliphatic higher alcohols; a monoglycidyl ether of phenol, cresol, butyl phenol or a polyether alcohol obtained by adding an alkylene oxide thereto; glycidyl esters of higher fatty acids; epoxidized soybean oil, octyl epoxystearate, butyl epoxystearate, and epoxidized polybutadiene.

The amount of the curing agent in the epoxy resin curing composition of the invention is not particularly limited. The curing agent is usually used in an amount such that the ratio of the total number of moles of epoxy groups of the epoxy compound to the number of functional groups of the curing agent ranges from 0.9/1.0 to 1.0/0.9. When the epoxy compound of the invention is used as an epoxy resin, the amount of the curing agent is preferably 30% to 80% by mass in the epoxy resin curing composition of the invention.

A fluorine-substituted curing agent is preferred; for it provides a cured epoxy resin with low water absorption. Being expensive in general, a fluorine-substituted compound should be selected as appropriate to the intended use of the product with other physical properties taken into consideration.

The epoxy resin curing composition of the invention may contain other known curing agents as a curing agent when in using the phenol compound of the invention (i.e., the phenol compound of general formula (I), e.g., compound Nos. 1 to 8), the phenol compound of general formula (II) (e.g., compound No. 9), the phenol compound of general formula (III)

(e.g., compound No. 10-1) or the phenol compound of general formula (IV) (e.g., compound No. 10-2) as a curing agent as well as using the epoxy compound (i.e., the epoxy compound of general formula (I) (e.g., compound Nos. 11-18), the epoxy compound of general formula (II) (e.g., compound No. 19), the epoxy compound of general formula (III) (e.g., compound No. 20-1), or the epoxy compound of general formula (IV) (e.g., compound No. 20-2) as an epoxy compound.

A combined use of other known curing agent(s) is expected to help control the viscosity or curing characteristics of the curing composition or the physical properties after cure. Examples of useful other curing agents are latent curing agents, polyamine compounds, polyphenol compounds, and cationic photoinitiators.

Examples of the latent curing agents include dicyandiamides, hydrazides, imidazole compounds, amine adducts, sulfonium salts, onium salts, ketimines, acid anhydrides, and tertiary amines. These latent curing agents are preferred; for they provide an easy-to-handle one-pack type curing composition.

Examples of the acid anhydrides include phthalic anhydride, trimellitic anhydride, pyromellitic anhydride, tetrahydrophthalic anhydride, hexahydrophthalic anhydride, maleic anhydride, succinic anhydride, and 2,2-bis(3,4-dicarboxyphenyl)-1,1,1,3,3,3-hexafluoroprpane dianhydride.

Examples of the polyamine compounds include aliphatic polyamines such as ethylenediamine, diethylenetriamine, and triethylenetetramine; alicyclic polyamines such as menthenediamine, isophoronediamine, bis(4-amino-3-methylcyclohexyl)methane, bis(aminomethyl)cyclohexane, and 3,9-bis(3-aminopropyl)2,4,8,10-tetraoxaspiro[5,5]undecane; aliphatic amines having an aromatic ring such as m-xylenediamine; and aromatic polyamines such as m-phenylenediamine, 2,2-bis(4-aminophenyl)propane, diaminodiphenylmethane, diaminodiphenylsulfone, α,α-bis(4-aminophenyl)-p-diisopropylbenzene, and 2,2-bis(4-aminophenyl)-1,1,1,3,3,3-hexafluoropropane.

Examples of the polyphenol compounds include phenol novolak, o-cresol novolak, t-butylphenol novolak, dicyclopentadienecresol, terpenediphenol, terpenedicatechol, 1,1,3-tris(3-tert-butyl-4-hydroxy-6-methylphenyl)butane, butylidenebis(3-tert-butyl-4-hydroxy-6-methylphenyl), and 2,2-bis(4-hydroxyphenyl)-1,1,1,3,3,3-hexafluoropropane. Phenol novolak is preferred; for the resulting epoxy resin has suitable electrical characteristics and mechanical strength for use in laminated sheets.

The cationic photoinitiator that can be used in the invention is a compound capable of releasing a substance that induces cationic polymerization on being irradiated with energy rays. Preferred cationic photoinitiators are double salts which are onium salts capable of releasing a Lewis acid on being irradiated and their derivatives. Such compounds are typified by salts between a cation and an anion represented by general formula: $[A]^{m+}[B]^{m-}$.

The cation $[A]^{m+}$ is preferably an onium ion, which is represented by, for example, general formula $[(R^1)_aQ]^{m+}$, wherein $R^1$ is an organic group that contains 1 to 60 carbon atoms and may contain any number of atoms other than carbon; a is an integer of 1 to 5; when a is 2 or greater, a plurality of $R^{19}$s may be the same or different, and at least one of them is preferably the organic group which has an aromatic ring; Q is an atom or an atomic group selected from the group consisting of S, N, Se, Te, P, As, Sb, Bi, O, I, Br, Cl, F, and N=N; and m is a number satisfying relation: m=a−q, wherein q is the valence of Q in the cation $[A]^{m+}$, provided that the valence of N=N is taken as 0.

The anion $[B]^{m-}$ is preferably a halide complex ion, which is represented by, for example, general formula $[LX_b]^{m-}$, wherein L is a metal or metalloid, a center atom of the halide complex, selected from B, P, As, Sb, Fe, Sn, Bi, Al, Ca, In, Ti, Zn, Sc, V, Cr, Mn, Co, etc.; X is a halogen atom; b is an integer of 3 to 7; and m is a number satisfying relation: m=b−p, wherein p is the valence of L in the anion $[B]^{m-}$.

Examples of the anion $[LX_b]^{m-}$ include a tetrafluoroborate anion $(BF_4)^-$, a hexafluorophosphate anion $(PF_6)^-$, a hexafluoroantimonate anion $(SbF_6)^-$, a hexafluoroarsenate anion $(AsF_6)^-$, and a hexachloroantimonate anion $(SbCl_6)^-$.

Anions represented by $[LX_{b-1}(OH)]^{m-}$ are also preferred as an anion $B^{m-}$, wherein L, X, and b are as defined above. Other useful anions are a perchlorate ion $(ClO_4)^-$, a trifluoromethylsulfite ion $(CF_3SO_3)^-$, a fluorosulfonate ion $(FSO_3)^-$, a toluenesulfonate anion, and a trinitrobenzenesulfonate anion.

Of the above described onium salts particularly preferred are aromatic onium salts (a) to (c) below, which may be used individually or as a mixture of two or more thereof.

(a) Aryldiazonium salts including phenyldiazonium hexafluorophosphate, 4-methoxyphenyldiazonium hexafluoroantimonate, and 4-methylphenyldiazonium hexafluorophosphate.

(b) Diaryliodonium salts including diphenyliodonium hexafluoroantimonate, di(4-methylphenyl)iodonium hexafluorophosphate, and di(4-tert-butylphenyl)iodonium hexafluorophosphate.

(c) Triarylsulfonium salts including triphenylsulfonium hexafluoroantimonate, tris(4-methoxyphenyl)sulfonium hexafluorophosphate, diphenyl-4-thiophenoxyphenylsulfonium hexafluoroantimonate, diphenyl-4-thiophenoxyphenylsulfonium hexafluorophosphate, 4,4'-bis(diphenylsulfonio) phenyl sulfide bis(hexafluoroantimonate), 4,4'-bis (diphenylsulfonio)phenyl sulfide bis(hexafluorophosphate), 4,4'-bis[di(β-hydroxyethoxy)phenylsulfonio]phenyl sulfide bis(hexafluoroantimonate), 4,4'-bis[di(β-hydroxyethoxy) phenylsulfonio]phenyl sulfide bis(hexafluorophosphate), 4-[4'-(benzoyl)phenylthio]phenyl-di(4-fluorophenyl)sulfonium hexafluoroantimonate, and 4-[4'-(benzoyl)phenylthio] phenyl-di(4-fluorophenyl)sulfonium hexafluorophosphate.

In addition to the compounds (a) to (c), also preferred are iron arene complexes, such as $(\eta^5$-2,4-cyclopentadien-1-yl) [(1,2,3,4,5,6-η)-(1-methylethyl)benzene]iron hexafluorophosphate, and mixtures of an aluminum complex, such as tris(acetylacetonato)aluminum, tris(ethylacetonatoacetato) aluminum or tris(salicylaldehydato)aluminum, and a silanol, such as triphenylsilanol.

Especially preferred of the recited compounds are aromatic iodonium salts, aromatic sulfonium salts, and iron arene complexes from the standpoint of practical utility and photo sensitivity.

The photo initiator may be used in combination with one or more known photo polymerization accelerators such as benzoic acid compounds and tertiary amine compounds. The photo initiator is preferably used in an amount of 0.1% to 30% by weight based on the curing composition of the invention. Amounts less than 0.1% by weight can fail to produce effect of addition. Amounts more than 30% by weight can result in reduction of mechanical strength of a cured product.

Known light sources, such as a high pressure mercury lamp, a metal halide lamp, and a xenon lamp, can be used in the polymerization using the photo initiator. Irradiation with active energy rays, such as ultraviolet rays, electron beams, X-rays, radial rays, and radiofrequency waves using these light sources causes the photo initiator to release a Lewis acid, whereby the epoxy compound is cured. Light sources having a wavelength of 400 nm or shorter are effective.

The epoxy resin curing composition of the invention containing the curing agent (phenol compound) represented by general formula (I), (II), (III) or (IV) can be cured by any method known for conventional epoxy resins, such as curing with a curing agent, curing by self-polymerization using a curing catalyst, photo curing using a photo initiator, and curing rate control by a combined use of a cure accelerator.

The epoxy resin curing composition preferably further contains a fibrous filler, such as glass fiber, aluminum borate whisker, or boron nitride whisker, or a spherical filler, such as silica or alumina, according to necessity. In using fibrous fillers, the longer axis length and the aspect ratio are selected as appropriate for the intended use. In using spherical fillers, particles having a true spherical shape and a small diameter are preferred.

The epoxy resin curing composition of the present invention can be diluted with an appropriate solvent, such as propylene glycol monomethyl ether, into varnish, which can be infiltrated into a porous glass substrate, such as glass nonwoven fabric or glass woven fabric, followed by heating to produce a prepreg in a usual manner. A plurality of the prepregs are stacked one on top of another to prepare a laminated sheet. Copper foil is superposed on one or both sides of the resulting laminated sheet, followed by pressing under heat to provide a copper-clad glass epoxy laminate. A circuit pattern is formed on the copper-clad laminate (inner lamina), and the unnecessary part of the copper is etched out. Another prepreg and copper foil are superposed on at least one side of the inner lamina, followed by heat pressing at 170° C. and 40 kg/cm² for 90 minutes to give a multilayer laminate in a usual manner. Through-holes are drilled in the copper-clad laminate or multilayer laminate, and the inner wall of the throughholes are metallized (through-hole plating) to complete circuit formation in a usual manner thereby to provide a PWB.

The epoxy resin curing composition of the invention is useful in a variety of applications contemplated for known epoxy resins such as various electric and electronic materials, coatings (powder coatings, anticorrosion coatings, etc.), adhesives, building materials, and so forth, including copper-clad laminates, prepregs and PWBs used to make electronic printed circuit boards as illustrated above, sealants, casting materials, adhesives, and electrical insulating coatings.

The novel benzoxazole compound represented by general formula (V) will then be described.

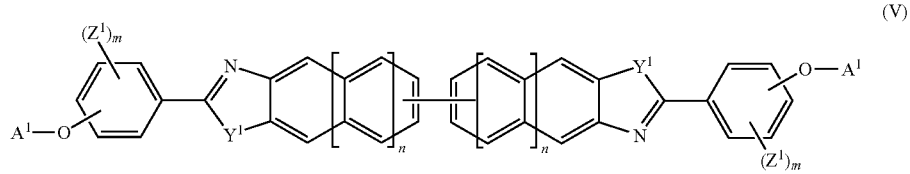

(V)

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a substituent having a phenolic hydroxyl group or a substituent having an epoxy group.

The term "substituent having a phenolic hydroxyl group" and the term "substituent having an epoxy group" as used in general formula (V) have the same meaning as respectively described as for general formula (I). Preference for these groups is the same as in general formula (I).

When the novel compound is a compound having a phenolic hydroxyl group, $A^1$ is a substituent having a phenolic hydroxyl group (including a phenol group). When the compound is a compound having an epoxy group, $A^1$ is a substituent having an epoxy group (including an epoxy group).

Specific examples of the novel compound having a phenolic hydroxyl group include compound Nos. 2 and 3 shown supra. Specific examples of the novel compound having an epoxy group include compound Nos. 11 to 13 shown supra. Understandably, these specific examples are only illustrative but not for limitation.

The novel compounds having a phenolic hydroxyl group and the novel compounds having an epoxy group can be synthesized by, for example, the processes previously described.

The novel compound is used in the epoxy resin curing composition of the invention as a curing agent for epoxy resins or as an epoxy resin. It is also useful in adhesive epoxy compositions, low linear expansion prepreg resins, and the like.

The novel benzoxazole compound represented by general formula (VI) is then described.

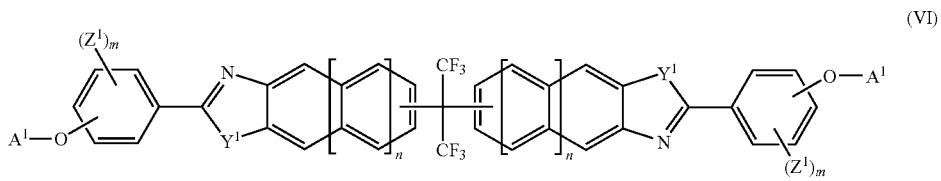

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a substituent having a phenolic hydroxyl group or a substituent having an epoxy group.

The term "substituent having a phenolic hydroxyl group" and the term "substituent having an epoxy group" as used in general formula (VI) have the same meaning as respectively described as for general formula (I). Preference for these groups is the same as in general formula (I).

When the novel compound is a compound having a phenolic hydroxyl group, $A^1$ is a substituent having a phenolic hydroxyl group (including a phenol group). When the compound is a compound having an epoxy group, $A^1$ is a substituent having an epoxy group (including an epoxy group).

The novel compound having an epoxy group is exemplified by compound No. 14 shown supra. Understandably, the example is only illustrative but not for limitation.

The novel compounds having a phenolic hydroxyl group and the novel compounds having an epoxy group can be synthesized by, for example, the processes previously described.

Similarly to the novel benzoxazole compound of formula (V), the novel compound of formula (VI) is used in the epoxy resin curing composition of the invention as a curing agent for epoxy resins or as an epoxy resin and also useful in adhesive epoxy compositions, low linear expansion prepreg resins, and the like.

EXAMPLES

The present invention will now be illustrated in greater detail with reference to Examples, but it should be understood that the invention is not construed as being limited thereto.

Examples 1 to 10 illustrate syntheses of phenol compounds and syntheses of epoxy compounds using the phenol compounds. Epoxy resin curing compositions containing the resulting epoxy compounds were prepared in accordance with the formulation shown in Tables 1 and 2 described later. In Comparative Examples 1 to 3 comparative epoxy resin curing compositions containing comparative compounds were prepared in accordance with the formulations shown in Table 3. Specimens A to C were prepared from each curing composition according to the methods described below and tested to evaluate chemical resistance, glass transition temperature, linear expansion coefficient, tensile strength, elongation, solder heat resistance, and heat cycle resistance according to the test methods described below. The results obtained are shown in Tables 1 to 3. Curing agents 1 to 3 used are shown below.

Curing agent 1

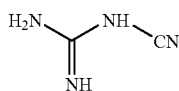

Curing agent 2

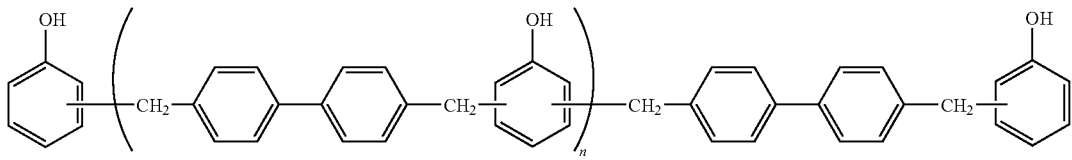

Curing agent 2 had an OH equivalent of 270 g/equiv.

Curing agent 3

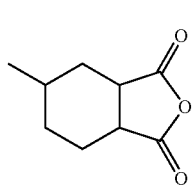

Example 1

Synthesis of Phenol Compound No. 2 and Synthesis of Epoxy Compound No. 12 using Compound No. 2

Phenol compound No. 2 was prepared, from which epoxy compound No. 12 was obtained.

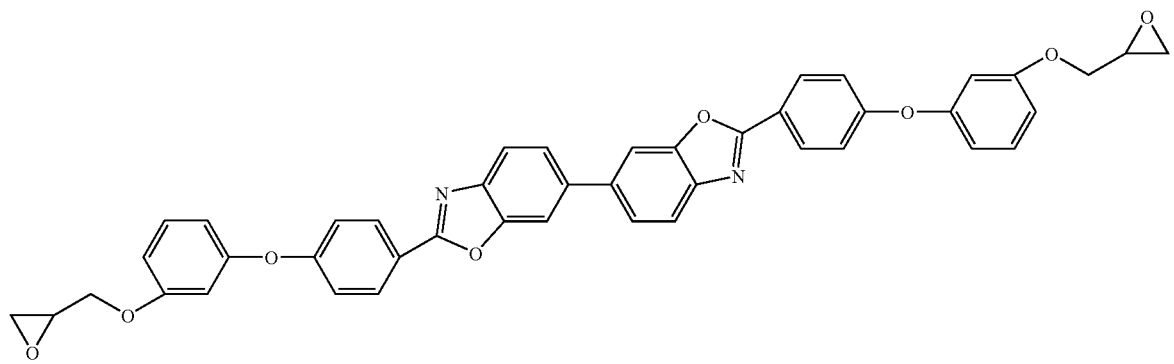

Compound No. 12

(1) Synthesis of Phenol Compound No. 2

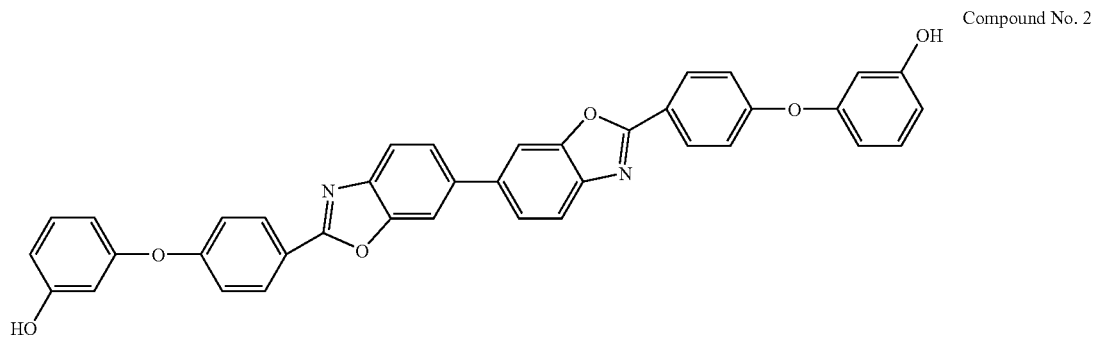

Compound No. 2

In a 200 ml four-necked flask were charged 21.624 g (0.10 mol) of 3,3'-dihydroxybenzidine, 29.42 g (0.21 mol) of 4-fluorobenzoic acid, and 65 ml of N-cyclohexyl-2-pyrrolidone in a nitrogen stream, and amidation reaction was conducted at 130° to 140° C. for 24 hours. The reaction mixture was heated up to 260° C., at which it was maintained for 2 hours, during which an additional 5 g of 4-fluorobenzoic acid was added, followed by continuing the reaction at 260° C. for 24 hours. After cooling, the precipitated yellow crystals were collected by filtration and washed with 50 ml of methanol to give 28.4 g of 2,2'-bis(4-fluorophenyl)bibenzoxazole.

In a 100 ml four necked flask were put 6.36 g (0.015 mol) of 2,2'-bis(4-fluorophenyl)bibenzoxazole, 8.253 g (0.075 mol) of hydroquinone, 7.69 g (0.06 mol) of potassium carbonate, 40 ml of N-methylpyrrolidone (NMP), and 25 ml of toluene in a nitrogen stream, and the mixture was refluxed at 130° C. for 2 hours while driving distilled water out of the system. The temperature was elevated up to 160° C., at which the system was maintained for 6 hours while removing toluene. The reaction was further continued at 185° C. for 3 hours to give a yellow crude product. The crude product was poured into 800 ml of water, and dilute hydrochloric acid was added thereto dropwise to adjust to pH 7. After the neutralization, the reaction product was stirred in water for 2 hours, collected by filtration and dried under reduced pressure at 150° C. for 2 hours to yield 8.72 g of compound No. 2, which was a phenol compound.

(2) Synthesis of Epoxy Compound No. 12

In a 50 ml three necked flask were put 2.0 g (0.0033 mol) of compound No. 2 obtained in (1) above, 0.264 g (0.0066 mol) of NaOH, 10 g of water, and 10.0 g of dimethyl sulfoxide (DMSO) in a nitrogen stream, and the mixture was heated up to 60° C., at which the mixture was stirred to dissolve. To the mixture was added dropwise 1.647 g (0.007 mol) of epichlorohydrin, and the reaction system was kept at 80° C. for 3 hours. After cooling, the precipitated yellow epoxidized product was collected by filtration, washed with 100 ml of water and 100 ml of methanol, and dried under reduced pressure at 150° C. for 2 hours to afford 2.38 g of compound No. 12, which was an epoxy compound. The IR chart of the resulting compound No. 12 is shown in FIG. 2. Compound No. 12 had an epoxy equivalent of 358 g/equiv.

Example 2

Synthesis of Phenol Compound No. 3 and Synthesis of Epoxy Compound No. 13 Using Compound No. 3

Phenol compound No. 3 was prepared, from which epoxy compound No. 13 was obtained.

Compound No. 13

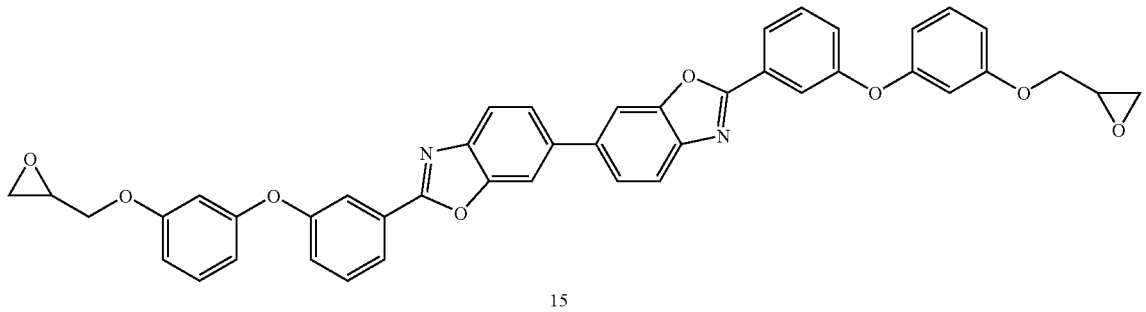

(1) Synthesis of Phenol Compound No. 3

Compound No. 3

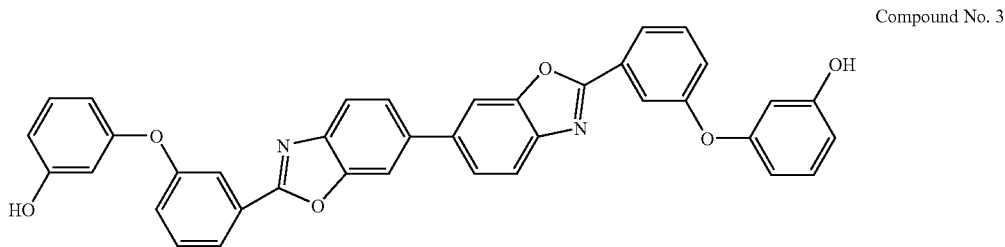

In a 200 ml four-necked flask were charged 21.624 g (0.10 mol) of 3,3'-dihydroxybenzidine, 29.42 g (0.21 mol) of 4-fluorobenzoic acid, and 65 ml of N-cyclohexyl-2-pyrrolidone in a nitrogen stream, and amidation reaction was conducted at 130° to 140° C. for 24 hours. The reaction mixture was heated up to 260° C., at which it was maintained for 2 hours, during which an additional 5 g of 4-fluorobenzoic acid was added, followed by continuing the reaction at 260° C. for 24 hours. After cooling, the precipitated yellow crystals were collected by filtration and washed with 50 ml of methanol to give 28.4 g of 2,2'-bis(4-fluorophenyl)bibenzoxazole.

In a 100 ml four necked flask were put 6.36 g (0.015 mol) of 2,2'-bis(4-fluorophenyl)bibenzoxazole, 8.253 g (0.075 mol) of resorcinol, 7.69 g (0.06 mol) of potassium carbonate, 40 ml of N-methylpyrrolidone (NMP), and 25 ml of toluene in a nitrogen stream, and the mixture was refluxed at 130° C. for 2 hours while driving distilled water out of the system. The temperature was elevated up to 160° C., at which the system was maintained for 6 hours while removing toluene. The reaction was further continued at 185° C. for 3 hours to give a yellow crude product. The crude product was poured into 800 ml of water, and dilute hydrochloric acid was added thereto dropwise to adjust to pH 7. After the neutralization, the reaction product was stirred in water for 2 hours, collected by filtration, and dried under reduced pressure at 150° C. for 2 hours to yield 8.72 g of compound No. 3, which was a phenol compound.

(2) Synthesis of Epoxy Compound No. 13

In a 50 ml three necked flask were put 2.0 g (0.0033 mol) of compound No. 3 obtained in (1) above, 0.264 g (0.0066 mol) of NaOH, 10 g of water, and 10.0 g of dimethyl sulfoxide (DMSO), and the mixture was heated up to 60° C., at which the mixture was stirred to dissolve. To the mixture was added dropwise 1.647 g (0.007 mol) of epichlorohydrin, and the reaction mixture was kept at 80° C. for 3 hours. After cooling, the precipitated yellow epoxidized product was collected by filtration, washed with 100 ml of water and 100 ml of methanol, and dried under reduced pressure at 150° C. for 2 hours to afford 2.38 g of compound No. 13, which was an epoxy compound. The IR chart of the resulting compound No. 13 is shown in FIG. 3. Compound No. 13 had an epoxy equivalent of 358 g/equiv.

Example 3

Synthesis of Phenol Compound No. 1 and Synthesis of Epoxy Compound No. 11 Using Compound No. 1

Epoxy compound No. 11 was synthesized from phenol compound No. 1 in the same manner as in Example 1. Phenol Compound No. 1 was prepared in the same manner as in Example 1.

Compound No. 11

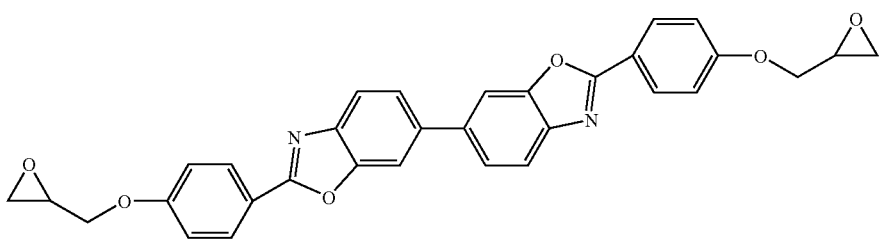

The compound No. 11 had an epoxy equivalent of 266 g/equiv.

Compound No. 1

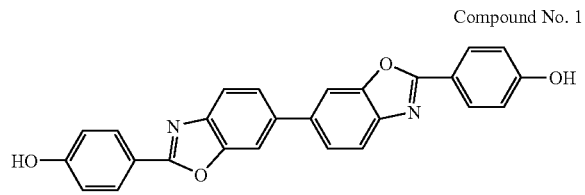

Example 4

Synthesis of Phenol Compound No. 7 and Synthesis of Epoxy Compound No. 17 Using Compound No. 7

Epoxy compound No. 17 was synthesized from phenol compound No. 7 in the same manner as in Example 1. Phenol Compound No. 7 was prepared in the same manner as in Example 1.

Compound No. 17

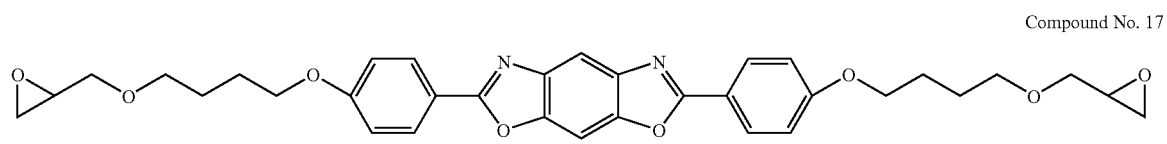

The compound No. 17 had an epoxy equivalent of 300 g/equiv.

Compound No. 7

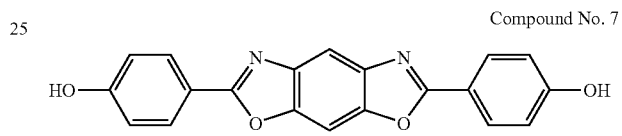

Example 5

Synthesis of Phenol Compound No. 4 and Synthesis of Epoxy Compound No. 14 Using Compound No. 4

Phenol compound No. 4 was prepared, from which epoxy compound No. 14 was obtained.

Compound No. 14

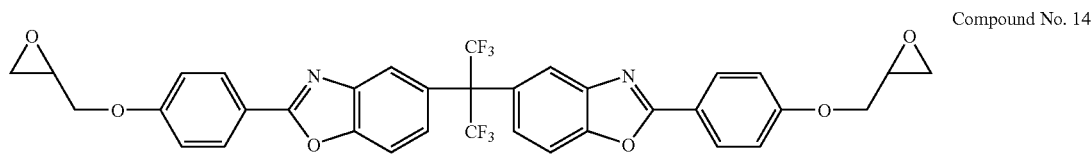

(1) Synthesis of Phenol Compound No. 4

Compound No. 4

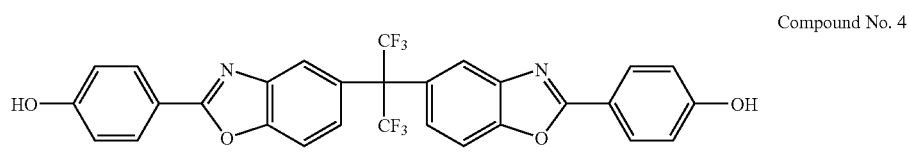

In 200 ml four necked flask were put 39.23 g (0.1 mol) of 2,2-bis(3-amino-4-hydroxyphenylhexafluoropropane) and 44.99 g (0.21 mol) of phenyl p-hydroxybenzoate in a nitrogen stream, and the mixture was heated to 150° C. The reaction system was evacuated and heated up to 180° C. while distilling off phenol, at which the system was maintained for 3 hours. After returning to atmospheric pressure, the system was heated to 240° C. to cause dehydrating ring closure for 20 hours. The reaction product was dissolved in 100 g of NMP, and the solution was poured into 1000 ml of water to reprecipitate. The crystals were collected by filtration, washed with ion exchanged water and methanol, and dried at 120° C. for 3 hours to give 50 g of compound No. 4, which was a phenol compound, in a yield of 83.8%. The IR chart of the resulting compound No. 4 is shown in FIG. 4.

(2) Synthesis of Epoxy Compound No. 14

In 200 ml of epichlorohydrin was dissolved 20 g of compound No. 4 obtained in (1) above, and 5.59 g of 48% sodium hydroxide was added thereto to induce etherification and ring closure to yield compound No. 14. The IR chart of the resulting compound No. 14 is shown in FIG. 5. The compound No. 14 had an epoxy equivalent of 341 g/equiv.

Example 6

Synthesis of Phenol Compound No. 5 and Synthesis of Epoxy Compound No. 15 Using Compound No. 5

Epoxy compound No. 15 was synthesized from phenol compound No. 5 in the same manner as in Example 1. Phenol Compound 5 was prepared in the same manner as in Example 1.

Compound No. 15

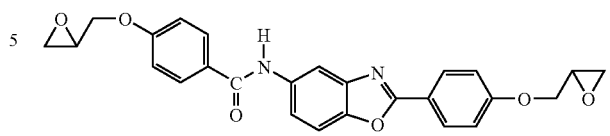

The compound No. 15 had an epoxy equivalent of 229 g/equiv.

Compound No. 5

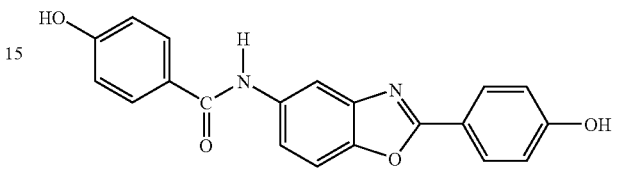

Example 7

Synthesis of Phenol Compound No. 6 and Synthesis of Epoxy Compound No. 16 Using Compound No. 6

Epoxy compound No. 16 was synthesized from phenol compound No. 6 in the same manner as in Example 1. Phenol Compound 6 was prepared in the same manner as in Example 1.

Compound No. 16

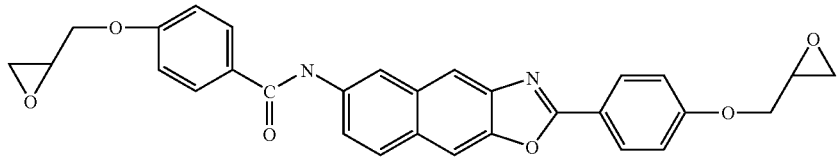

The compound No. 16 had an epoxy equivalent of 254 g/equiv.

Compound No. 6

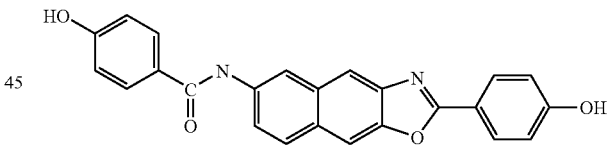

Example 8

Synthesis of Phenol Compound No. 8 and Synthesis of Epoxy Compound No. 18 Using Compound No. 8

Epoxy compound No. 18 was synthesized from phenol compound No. 8 in the same manner as in Example 1. Phenol Compound 8 was prepared in the same manner as in Example 1.

Compound No. 18

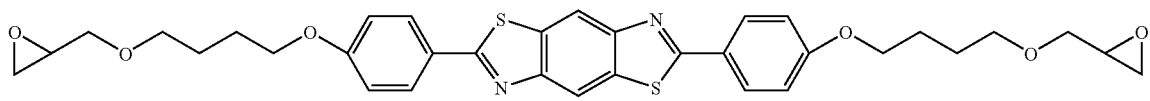

The compound No. 18 had an epoxy equivalent of 316 g/equiv.

Compound No. 8

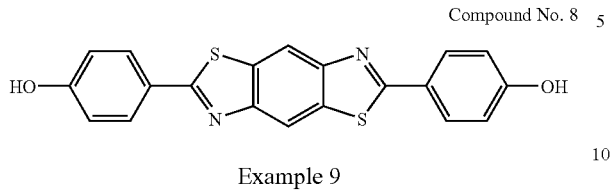

Example 9

Synthesis of Phenol Compound No. 9 and Synthesis of Epoxy Compound No. 19 Using Compound No. 9

Epoxy compound No. 19 was synthesized from phenol compound No. 9 in the same manner as in Example 1. Phenol Compound 9 was prepared as follows.

Compound No. 19

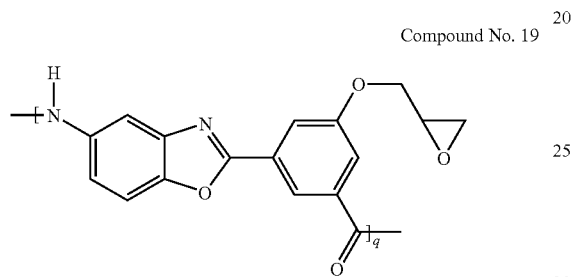

The compound No. 19 had an epoxy equivalent of 338 g/equiv.

Synthesis of Phenol Compound No. 9

Compound No. 9

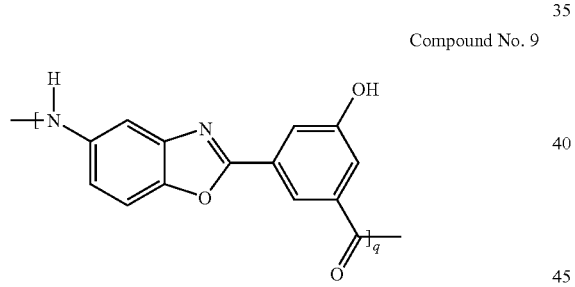

In a reactor were charged all at once 5.46 g (0.03 mol) of 5-hydroxyisophthalic acid, 5.91 g (0.03 mol) of amidol, 9.31 g (0.03 mol) of triphenyl phosphite, 2.54 g (0.06 mol) of lithium chloride, 37.8 g of N-methylpyrrolidone (NMP), and 9.45 g of pyridine and allowed to react at 100° C. for 3 hours. After the reaction, about 1.5 l of acetone was added. The precipitate thus formed was collected by filtration to obtain a crude product, which was washed with about 300 ml of boiling acetone for 30 minutes, filtered, dried in reduced pressure at 150° C. for 3 hours, and then dried in vacuo at 260° C. for 10 hours for ring closure to give compound No. 9, which was a phenol compound.

Example 10

Synthesis of Phenol Compound No. 10-1 and Synthesis of Epoxy Compound No. 20-1 Using Compound No. 10-1

Epoxy compound No. 20-1 was synthesized from phenol compound No. 10-1 in the same manner as in Example 1. Phenol Compound 10-1 was prepared as follows.

Compound No. 20-1

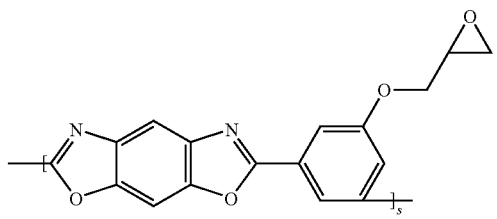

The compound No. 20-1 had an epoxy equivalent of 336 g/equiv.

Synthesis of Phenol Compound No. 10-1

Compound No. 10-1

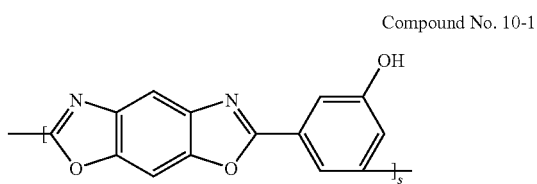

In a reactor were put all at once 5.46 g (0.03 mol) of 5-hydroxyisophthalic acid, 6.39 g (0.03 mol) of 4,6-diaminoresorcinol dihydrochloride, 9.31 g (0.03 mol) of triphenyl phosphite, 2.54 g (0.06 mol) of lithium chloride, 37.8 g of N-methylpyrrolidone (NMP), and 9.45 g of pyridine and allowed to react at 100° C. for 3 hours. After the reaction, about 1.5 l of acetone was added. The precipitate thus formed was collected by filtration to obtain a crude product, which was washed with about 300 ml of boiling acetone for 30 minutes, filtered, dried in reduced pressure at 150° C. for 3 hours, and then dried in vacuo at 260° C. for 10 hours for cyclization to give compound No. 10-1, which was a phenol compound.

Comparative Examples 1 to 5

Preparation of Epoxy Resin Curing Composition Containing Comparative Epoxy Compounds 1 to 5

A comparative epoxy resin curing composition containing each of comparative epoxy compounds 1 to 5 below was prepared in accordance with the formulation shown in Table 3. Specimens were prepared from the resulting composition and tested in the same manner as described above. The results obtained are shown in Table 3.

Comparative epoxy compound 1

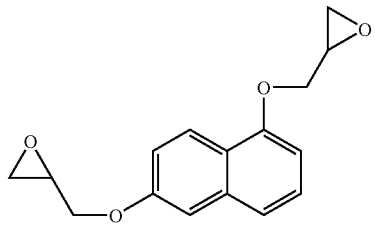

The comparative epoxy compound 1 had an epoxy equivalent of 136 g/equiv.

Comparative epoxy compound 2

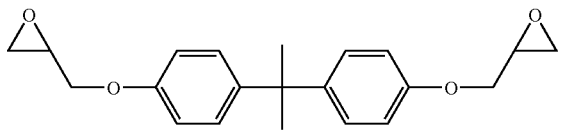

The comparative epoxy compound 2 had an epoxy equivalent of 170 g/equiv.

Comparative epoxy compound 3

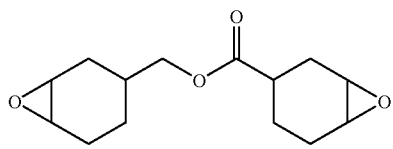

The comparative epoxy compound 3 had an epoxy equivalent of 126 g/equiv.

Comparative epoxy compound 4

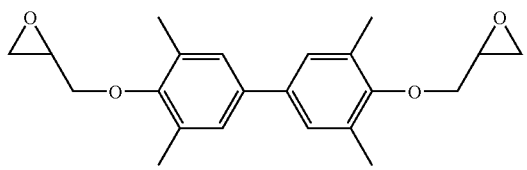

The comparative epoxy compound 4 had an epoxy equivalent of 180 g/equiv.

Compound epoxy compound 5

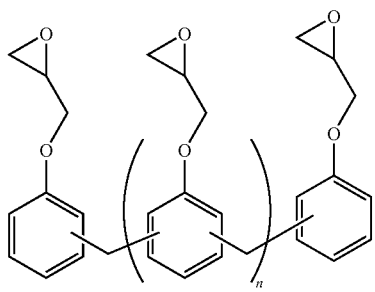

The comparative epoxy compound 5 had an epoxy equivalent of 162 g/equiv.

(1) Preparation of Specimen

Specimen A:

Each of the epoxy resin compositions of Examples and Comparative Examples was applied to a 38 μm thick PET release film to a thickness of 200 μm and dried in a heating oven at 130° C. for 10 minutes to obtain a B-stage dry film. The dry film was applied on its resin side to a release-treated glass substrate by vacuum lamination at 90° C. for 10 minutes. The PET film was stripped off to transfer the B stage resin film to the glass substrate. The B stage resin film on the glass substrate was completely cured in a heating oven at 150° C. for 1 hour. After cooling to room temperature, the completely cured resin film was released from the glass substrate to provide a specimen A (resin film).

Specimen B:

The test epoxy resin composition was applied to a matte side of a 12 μm thick electrolytic copper foil for PWBs to a thickness of 120 μm and dried in a heating oven at 130° C. for 10 minutes to prepare a B-stage resin-coated copper foil. The resin-coated copper foil was applied to both sides of a 0.1 mm thick double-sided glass epoxy core wiring board (FR-4) by vacuum pressing under conditions shown in FIG. 1, thereby to completely cure the resin to provide a specimen B.

Specimen C:

The specimen B was processed to prepare a 40 mm-side square wiring board having 70 μm diameter electrodes at a pitch of 120 μm. Separately, an LSI chip measuring 8.5 mm in length, 8.5 mm in width, and 0.06 mm in height and having 70 μm diameter gold bump electrodes at a pitch of 120 μm was prepared, and the test epoxy resin curing composition was applied to the peripheries of the electrodes of the LSI chip. The LSI chip was mounted on the wiring board with the electrodes of the chip and those of the wiring board brought into contact with each other. The chip on board assembly was heated in a heating oven at 150° C. for 1 hour to completely cure the resin, thereby to make a specimen C.

(2) Chemical Resistance Test

The specimen A was rubbed with a cotton swab moistened with NMP (N-methylpyrrolidone), and the number of rubs needed to make a scratch on the surface of the specimen was noted.

(3) Glass Transition Temperature (Tg)

A test piece of 5 mm by 50 mm was cut out of the specimen A with a cutter knife. Dynamic viscoelasticity of the cut piece was measured with DMS-6100 from SII NanoTechnology, Inc. The temperature at which tan δ peaks was taken as a glass transition temperature (Tg).

(4) Coefficient of Linear Expansion (CLE)

A test piece of 5 mm by 50 mm was cut out of the specimen A with a cutter knife. A thermal expansion curve of the cut piece was measured with TMA/SS6000 from SII NanoTechnology, Inc. A linear expansion coefficient was calculated from the linear extension in a temperature range of from 40° to 100° C.

(5) Tensile Strength and Elongation

Tensile strength and elongation were measuring using the specimen A in accordance with JIS K7127 (specimen type 5).

(6) Solder Heat Resistance Test (SHRT)

The specimen B cut into a 40 mm square was floated on a solder bath adjusted at 288° C. for 1 minute and inspected for any abnormality such as delamination. After the specimen was taken out of the solder bath and left to stand at room temperature for 1 minute, the same test was repeated ten times. The number of cycles the specimen withstood was determined.

(7) Heat Cycle Test (HCR)

After the specimen C was tested in accordance with IPC-D-275 (Test Condition E), the specimen was inspected for appearance and circuit resistivity change to see if any abnormality such as wiring break or crack or poor connection occurred.

TABLE 1

|  | Example 1 | Example 2 | Example 3 | Example 4 | Example 5 |
| --- | --- | --- | --- | --- | --- |
| Compound No. 12 | 10 g | | | | |
| Compound No. 13 | | 10 g | | | |
| Compound No. 11 | | | 10 g | | |
| Compound No. 17 | | | | 10 g | |
| Compound No. 14 | | | | | 10 g |
| Curing Agent 1 | 1.00 g | 1.00 g | 1.34 g | 1.19 g | 1.05 g |
| Curing Agent 2 | | | | | |
| Curing Agent 3 | | | | | |
| TPP | | | | | |
| NMP | 11.00 g | 11.00 g | 11.34 g | 11.19 g | 11.05 g |
| Chemical Resistance (time) | ≧100 | ≧100 | ≧100 | ≧100 | ≧100 |
| Tg. (° C.) | 180 | 175 | 195 | 160 | 180 |
| CLE (ppm) | 5.0 | 5.5 | 3.0 | 10.0 | 6.0 |
| Tensile Strength (Mpa) | 90 | 90 | 80 | 105 | 95 |
| Elongation (%) | 5.0 | 5.5 | 3.0 | 8.0 | 6.0 |
| SHRT (time) | 10 | 10 | 10 | 10 | 10 |
| HCT | NAD | NAD | NAD | NAD | NAD |

* TPP stands for triphenylphosphine.
NAD stands for no abnormality detected.

TABLE 2

|  | Example 6 | Example 7 | Example 8 | Example 9 | Example 10 |
| --- | --- | --- | --- | --- | --- |
| Compound No. 15 | 10 g | | | | |
| Compound No. 16 | | 10 g | | | |
| Compound No. 18 | | | 10 g | | |
| Compound No. 19 | | | | 10 g | |
| Compound No. 20-1 | | | | | 10 g |
| Curing Agent 1 | | | | | |
| Curing Agent 2 | 11.8 g | 10.6 g | 8.5 g | | |
| Curing Agent 3 | | | | 5.0 g | 5.0 g |
| TPP | 0.65 g | 0.62 g | 0.56 g | 0.45 g | 0.45 g |
| NMP | 22.45 g | 21.22 g | 19.06 g | 15.45 g | 15.45 g |
| Chemical Resistance (time) | ≧100 | ≧100 | ≧100 | ≧100 | ≧100 |
| Tg. (° C.) | 185 | 190 | 160 | 180 | 190 |
| CLE (ppm) | 15.0 | 12.0 | 18.0 | 5.0 | 5.0 |
| Tensile Strength (Mpa) | 80 | 85 | 100 | 90 | 80 |
| Elongation (%) | 3.0 | 3.5 | 4.5 | 4.0 | 3.0 |
| SHRT (time) | 10 | 10 | 10 | 10 | 10 |
| HCT | NAD | NAD | NAD | NAD | NAD |

TABLE 3

|  | Comparative Example 1 | Comparative Example 2 | Comparative Example 3 | Comparative Example 4 | Comparative Example 5 |
| --- | --- | --- | --- | --- | --- |
| Comparative Epoxy Compound 1 | 10 g | | | | |
| Comparative Epoxy Compound 2 | | 10 g | | | |
| Comparative Epoxy Compound 3 | | | 10 g | | |
| Comparative Epoxy Compound 4 | | | | 10 g | |
| Comparative Epoxy Compound 5 | | | | | 10 g |
| Curing Agent 1 | 2.62 g | 2.11 g | 2.83 g | 1.98 g | 2.20 g |
| Curing Agent 2 | | | | | |
| Curing Agent 3 | | | | | |
| TPP | | | | | |
| NMP | 12.62 g | 12.11 g | 12.83 g | 11.98 g | 12.20 g |
| Chemical Resistance (time) | ≧100 | ≧100 | ≧100 | ≧100 | ≧100 |
| Tg. (° C.) | 150 | 135 | 160 | 170 | 180 |
| CLE (ppm) | 50 | 60 | 55 | 50 | 50 |
| Tensile Strength (Mpa) | 80 | 80 | 85 | 75 | 70 |
| Elongation (%) | 3.0 | 4.0 | 5.0 | 2.5 | 2.0 |
| SHRT (time) | 1 | 0 | 1 | 2 | 2 |
| HCT | Break, crack, and poor connection detected. | | | | |

INDUSTRIAL APPLICABILITY

An epoxy resin curing composition that is free of a filler and yet excellent in physical properties including linear expansion coefficient, tensile strength, and elongation is provided by using the compound having a benzoxazole structure according to the invention as a curing agent or an epoxy resin.

The invention claimed is:

1. An epoxy resin curing composition comprising a compound having a benzoxazole structure represented by general formula (I):

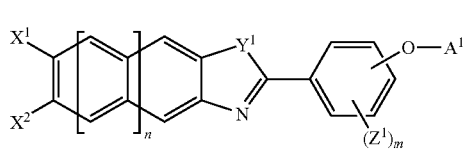

wherein $X^1$ and $X^2$, which may be the same or different, each independently represent a hydrogen atom, a substituent having a phenolic hydroxyl group, or a substituent having an epoxy group, with proviso that $X^1$ and $X^2$ do not represent a hydrogen atom at the same time; $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group, wherein either one of $X^1$ and $X^2$ in general formula (I) is represented by general formula (Ia):

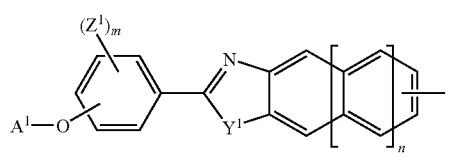

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

2. A curing composition for a laminated sheet comprising the epoxy resin curing composition according to claim 1.

3. An epoxy resin curing composition comprising a compound having a benzoxazole structure represented by general formula (I):

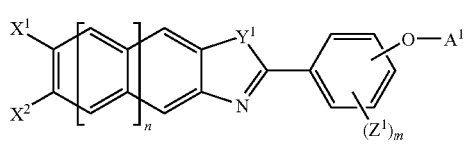

wherein $X^1$ and $X^2$, which may be the same or different, each independently represent a hydrogen atom, a substituent having a phenolic hydroxyl group, or a substituent having an epoxy group, with proviso that $X^1$ and $X^2$ do not represent a hydrogen atom at the same time; $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group, wherein either one of $X^1$ and $X^2$ in general formula (I) is represented by general formula (Ib):

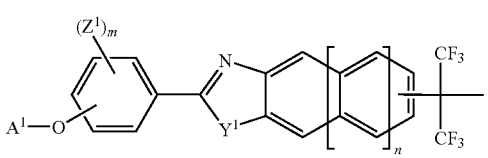

wherein $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; and $A^1$ represents a hydrogen atom, a substituent having a phenolic hydroxyl group or a substituent having an epoxy group.

4. A curing composition for a laminated sheet comprising the epoxy resin curing composition according to claim 3.

5. An epoxy resin curing composition comprising a compound having a benzoxazole structure represented by general formula (I):

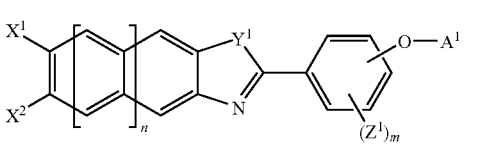

wherein $X^1$ and $X^2$, which may be the same or different, each independently represent a hydrogen atom, a substituent having a phenolic hydroxyl group, or a substituent having an epoxy group, with proviso that $X^1$ and $X^2$ do not represent a hydrogen atom at the same time; or $X^1$ and $X^2$ are linked to each other to form a 3- to 8-membered, saturated or unsaturated heterocyclic ring substituted with a substituent having a phenolic hydroxyl group or a substituent having an epoxy group; $Y^1$ represents an oxygen atom or a sulfur atom; $Z^1$ represents a substituted or unsubstituted hydrocarbon group having 1 to 8 carbon atoms or a substituted or unsubstituted alkoxy group having 1 to 8 carbon atoms; m represents an integer of 0 to 4; when m is 2 to 4, a plurality of $Z^1$s may be the same or different; n represents an integer of 0 to 2; wherein $A^1$ is a substituent having an epoxy group.

6. A curing composition for a laminated sheet comprising the epoxy resin curing composition according to claim 5.

* * * * *